(12) United States Patent
Kim et al.

(10) Patent No.: US 8,148,101 B2
(45) Date of Patent: Apr. 3, 2012

(54) METHOD FOR CLASSIFYING AND COUNTING BACTERIA IN BODY FLUIDS

(75) Inventors: Young Ran Kim, Sunnyvale, CA (US); Willie J. Cowart, San Francisco, CA (US)

(73) Assignee: Abbott Laboratories, Abbott Park, IL (US)

( * ) Notice: Subject to any disclaimer, the term of this patent is extended or adjusted under 35 U.S.C. 154(b) by 800 days.

(21) Appl. No.: 12/177,251

(22) Filed: Jul. 22, 2008

(65) Prior Publication Data

US 2010/0021878 A1    Jan. 28, 2010

(51) Int. Cl.
*C12Q 1/02* (2006.01)
(52) U.S. Cl. ............................................. 435/29; 435/2
(58) Field of Classification Search .................. 435/2, 29
See application file for complete search history.

(56) References Cited

U.S. PATENT DOCUMENTS

| | | | |
|---|---|---|---|
| 5,298,426 A | 3/1994 | Inami et al. | |
| 5,325,168 A | 6/1994 | Nakamoto et al. | |
| 5,516,695 A | 5/1996 | Kim et al. | |
| 5,534,416 A * | 7/1996 | Millard et al. | 436/34 |
| 5,559,037 A | 9/1996 | Kim et al. | |
| 5,631,165 A | 5/1997 | Chupp et al. | |
| 5,648,225 A | 7/1997 | Kim et al. | |
| 5,656,499 A | 8/1997 | Chupp et al. | |
| 5,939,326 A | 8/1999 | Chupp et al. | |
| 7,309,581 B2 | 12/2007 | Sakai et al. | |
| 7,468,789 B2 | 12/2008 | Czarnek | |
| 7,618,587 B2 | 11/2009 | Kawate | |
| 2007/0178533 A1 | 8/2007 | Poccia et al. | |

FOREIGN PATENT DOCUMENTS

| | | |
|---|---|---|
| EP | 1376135 B1 | 1/2004 |
| EP | 1376135 B1 | 2/2004 |
| EP | 1405918 B1 | 7/2004 |
| WO | 2005124350 A1 | 12/2005 |
| WO | 2006026109 A1 | 9/2006 |
| WO | 2007149407 A2 | 12/2007 |

OTHER PUBLICATIONS

Gant, VA et al. The application of flow cytometry to the study of bacterial responses to antibiotics. J. Med. Microbiol. 1993. 39: 147-154.*
Mansour, JD et al. Fluorescent staining of intracellular and extracellular bacteria in blood. Journal of Clinical Microbiology. 1984. 19(4): 453-456.*
Sugiuchi, H et al. Measurement of total and differential white blood cell counts in synovial fluid by means of an automated hematology analyzer. J. Lab. Clin. Med. 2005. 146(1): 36-42.*
N. Harris et al., The Advia 2120 Hematology System: Flow Cytometry-Based Analysis of Blood and Body Fluids in the Routine Hematology Laboratory, Laboratory Hematology 11, pp. 47-61, (c) 2005 Carden Jennings Publishing Co., Ltd.
W. Brown et al., Validation of Body Fluid Analysis on the Coulter LH 750, Laboratory Hematology 9, pp. 155-159, (c) 2003 Carden Jennings Publishing Co., Ltd.
L. Kresie et al., Performance Evaluation of the Application of Body Fluids on the Sysmex XE-2100 Series Automated Hematology Analyzer, Laboratory Hematology 11, pp. 24-30, (c) 2005 Carden Jennings Publishing Co., Ltd.
Hoffmann, et al., "Automated Counting of Cells in Cerebrospinal Fluid Using the CellDyn-4000 Haematology Analyser", Clin Chem Lab Med 2002; 40(11):1168-1173 © 2002 by Walter de Gruyter.
Hoffmann, et al., "Pseudo-reticulocytosis as a result of malaria parasites", Clin. Lab. Haem. 1999, 21, 257-260.
Kim, et al., "Effects of bacteria and yeast om WBC counting in three automated hematology counters", Ann Hematol (2008) 87:557-562.
Saito, et al., "Feasibility of flow cytometry for the detection of bacteria from body fluid samples", J Infect Chemother (2005) 11:220-225 © Japanese Society of Chemotherapy and the Japanese Association for Infections Diseases 2005.
Shapiro, H.M. ed. "Practical Flow Cytometry", Wiley-Liss (New York:1995) pp. 419-423.
Wever, et al., "Detection of Imported Malaria with the Cell-Dyn 4000 Hematology Analyzer", Journal of Clinical Microbiology, Dec. 2002, p. 4729-4731 © 2002, American Society for Microbiology.
The PCT International Search Report, PCT/US2009/051097, Date of mailing Dec. 18, 2009.
W. Williams. Hem I Automated Cell Counting and Evaluation. Educational publication [online], [retrieved on Jul. 15, 2008]. Retrieved from the Internet: URL: <http://www.clt.astate.edu/wwilliams/new_page_4.html>.

* cited by examiner

*Primary Examiner* — Allison Ford
*Assistant Examiner* — Susan E Fernandez
(74) *Attorney, Agent, or Firm* — Edward J. Baba; Peter A. Socarras; Bozicevic, Field & Francis LLP

(57) ABSTRACT

A method for distinguishing erythroblasts from bacteria by automated hematology analyzers, such as, for example, the CELL-DYN® 4000 automated hematology analyzer and the CELL-DYN® Sapphire™ automated hematology analyzer. Bacterial cells scatter light and fluoresce differently than do red blood cells, white blood cells, erythroblast nuclei, and platelets. Signals generated by bacteria are distinguishable from those of erythroblasts because the signals generated by erythroblast nuclei are sufficiently unique that erythroblast nuclei can be distinguished from signals generated by bacteria. Signals generated by platelets, lysed red blood cell ghosts, and other cell debris are blocked by the triple-trigger circuitry of the hematology analyzer, because all of the signals generated by noise are below the AND/OR thresholds. Algorithm(s) in the software of the system detect and count signals generated by bacteria by means of the location and the shape of the signals generated by bacteria and calculate the concentration of bacteria per unit of body fluid. In addition, certain body fluids, such as, for example, synovial fluid, can be pretreated with a viscosity reducing agent for a short period of time to reduce the viscosity of the body fluid prior to analyzing a sample of the body fluid by an automated hematology analyzer.

20 Claims, 17 Drawing Sheets

METHOD FOR CLASSIFYING AND COUNTING BACTERIA IN BODY FLUIDS

BACKGROUND OF THE INVENTION

1. Field of the Invention

This invention relates to a method for classifying and counting white blood cells, erythroblasts, and bacteria in body fluids by means of an automated hematology analyzer. More particularly, this invention relates to a method for simultaneously differentiating and counting white blood cell populations, erythroblasts, and bacteria in body fluids by means of multi-angle light scatter, fluorescence, and triple triggering circuitry in a three-dimensional space.

2. Discussion of the Art

Examination of various body fluids is critical for the diagnosis of bacterial meningitis, bacterial pneumonia or lung abscess, infection of the peritoneal cavity, and septic arthritis. The conventional method of analyzing body fluids in order to determine the presence of a bacterial infection, which involves dilution of biological samples, counting cells by means of a hemocytometer, preparing cell cultures, Gram staining, and microscopic examination, is tedious, time-consuming, and labor-intensive, and some clinical cases, such as bacterial meningitis, require immediate treatment because an untreated case can be lethal. Thus, the ability to analyze body fluids on a rapid hematology analyzer would be extremely useful.

Analysis of most body fluids drawn from hospitalized patients must be carried out in the hospital as soon as possible because such body fluids are not very stable and can be expected to deteriorate within approximately two hours. Cerebrospinal fluid can be expected to deteriorate within one hour. See, for example, Body Fluids: Laboratory examination of amniotic, cerebrospinal, seminal, serous, & synovial fluids: a text book atlas/C. Kjeldsberg and J. Knight, eds. $3^{rd}$ ed. ASCP Press, 1993, incorporated herein by reference. Thus, analyzing body fluids rapidly on an automated hematology analyzer would be desirable in hospital laboratories.

A number of manufacturers of hematology analyzers have systems that use the analysis of body fluids for cell counting. The Beckman-Coulter LH 750 hematology analyzer uses VCS technology (Volume by impedance, Complexity by radio-frequency, and laser light Scatter) for analysis of white blood cell differential. However, VCS technology cannot discriminate signals generated by bacterial cells from signals generated by other cell debris. The Bayer ADVIA® 2120 hematology analyzer uses myelo-peroxidase staining and light scatter to differentiate white blood cells. In the basophil channel, also known as the Lobularity/Nuclear density channel, a hypotonic surfactant solution is used to strip the cytoplasmic membrane from all leukocytes, except basophils. Neither the myeloperoxidase channel nor the basophil channel of the ADVIA® 2120 hematology analyzer is capable of distinguishing the signals generated by bacteria from signals generated by erythroblast nuclei or other cell debris.

The Sysmex XE-2100 hematology analyzer uses forward light scatter and side light scatter for counting white blood cells and nuclear staining, and side light scatter and fluorescence for differential analysis. However, the analyzer cannot distinguish the small noise signals generated by cell debris from those generated by bacteria. U.S. Pat. No. 5,325,168 describes a method and apparatus for analyzing cells in urine using both light scatter for determining size and fluorescence for determining differential DNA-staining intensity. This patent does not disclose how signals generated by small bacteria can be distinguished from noise signals generated by cell debris or from erythroblast nuclei. The cytograms of light scatter vs. fluorescence, i.e., FIGS. 14A, 14B, and 14C of U.S. Pat. No. 5,325,168, show no noticeable separation of noise signals from small bacterial signals.

To resolve the problems stated above, a rapid analysis of body fluids by means of an automated hematology analyzer, available in most clinical laboratories, is highly desirable to save the lives of infected patients by the rapid diagnosis of the medical condition of the patients and the subsequent treatment of the patients.

SUMMARY OF THE INVENTION

It has been discovered that the signatures of erythroblasts from certain automated hematology analyzers, such as, for example, the CELL-DYN® 4000 automated hematology analyzer and the CELL-DYN® Sapphire™ automated hematology analyzer, are readily distinguishable from the signatures of bacteria, i.e., bacterial cells scatter light and fluoresce differently than do red blood cells, white blood cells, erythroblast nuclei, and platelets. The CELL-DYN® Sapphire™ automated hematology analyzer, as well as the CELL-DYN® 4000 automated hematology analyzer, both of which are commercially available from Abbott Laboratories, are equipped with an optical bench that can measure multi-angle light scatter and fluorescence, as described in U.S. Pat. Nos. 5,631,165 and 5,939,326, both of which are incorporated herein by reference. Furthermore, U.S. Pat. Nos. 5,516,695 and 5,648,225, both of which are incorporated herein by reference, describe a reagent suitable for lysing red blood cells and staining nuclear DNA of membrane lysed erythroblasts to discriminate white blood cells from erythroblasts. Membrane lysed erythroblasts are erythroblasts wherein the membrane thereof has undergone lysis. U.S. Pat. No. 5,559,037, incorporated herein by reference, describes the simultaneous detection of erythroblasts and white blood cell differential by means of a triple triggering circuitry (AND/OR), which is used to eliminate noise signals from cell debris, such as, for example, membranes of lysed red blood cells, which are located below the lymphocyte cluster along the Axial Light Loss (ALL) axis of a cytogram.

Most hematology analyzers are not capable of distinguishing signals generated by bacteria from other components of a sample of a body fluid, such as, for example, red blood cell ghosts, platelets, and other cell debris.

This invention provides a method of differentiating and counting bacteria (microorganisms) in body fluids. In one aspect, the method comprises the steps of:

(a) providing an automated hematology analyzer capable of measuring multi-angle light scatter and fluorescence, the automated hematology analyzer having a triple-triggering system;

(b) providing a reagent capable of lysing red blood cells, the reagent also capable of preserving morphology of white blood cells;

(c) providing a sample of a body fluid;

(d) mixing the reagent and the sample of the body fluid;

(e) simultaneously lysing red blood cells and membranes of erythroblasts, if red blood cells and erythroblasts are present in the body fluid;

(f) staining erythroblast nuclei with a nuclear stain, if erythroblasts are present in the body fluid;

(g) differentiating white blood cells by means of multi-angle light scatter;

(h) detecting erythroblast nuclei by means of at least one of multi-angle light scatter and fluorescence, if erythroblasts are present in the body fluid; and (i) differentiating and counting bacteria by circuitry comprising detectors that measure fluorescence and multi-angle light scatter.

The method described herein can include the step of diluting a portion of the sample of the body fluid with a diluent to enable a minimal number of cells to pass through a counting aperture at the same time. The diluent is typically used for the channel that counts red blood cells. The method can also include the step of detecting and counting red blood cells, typically, but not necessarily, by an impedance measurement. The lysed sample of the body fluid is transported through a flow cell to measure multi-angle light scatter and fluorescence. The method described herein can further include the steps of (a) storing data for the analysis of the sample of the body fluid, (b) reporting results for the analysis of the sample of the body fluid, and (c) analyzing the sample of the body fluid by at least one algorithm to differentiate white blood cells, erythrocytes, and bacteria.

Signals generated by bacteria are distinguishable from those of erythroblasts because the signals generated by erythroblast nuclei are sufficiently unique that erythroblast nuclei can be distinguished from signals generated by bacteria. Signals generated by platelets, lysed red blood cell ghosts, and other cell debris are blocked by the triple-trigger circuitry of the hematology analyzer, because all of the signals generated by noise are below the AND/OR thresholds. Algorithm(s) in the software of the system detect and count signals generated by bacteria by means of the location and the shape of the signals generated by bacteria and calculate the concentration of bacteria per unit of body fluid.

In one embodiment, body fluids are analyzed without any manual preparation in the Open Mode of the hematology analyzer. The reagent system was originally developed to preserve white blood cells and their cell surface antigens thereof for immuno-phenotyping and, at the same time, lyse red blood cells and the membranes of erythroblasts and stain their nuclei for the detection of erythroblasts, as described in U.S. Pat. Nos. 5,516,695 and 5,648,225, both of which are incorporated herein by reference. In order to use this reagent system for analysis of bacteria, the samples prepared for the hematology analyzer by the reagent system are passed through the electro-optical system described in U.S. Pat. No. 5,656,499, incorporated herein by reference, in single file, whereupon the electronic logic of the system, triple-triggering circuitry, and the algorithm(s) of the system differentiate each cell population based on volume of the cells, complexity of the cells, lobularity of the cells, refractive index of the cells, fluorescence intensity of the cells, and the location and pattern of each cluster of cells. The triple-triggering circuitry eliminates signals from the cell debris and qualifies signals from white blood cells, erythroblasts, and bacteria. To be qualified as a valid bacterial signal, i.e., a signal generated by bacteria, the amplitude of the signal must be below the OR gate, ALL trigger, but above the AND gate, FL3 and IAS triggers; the algorithm(s) of the system carry out the function of differentiating bacterial signals from signals generated by erythroblasts by the size of the ALL signal, the intensity of the FL3+ signals from bacteria, and the shape and the number of FL3 clusters, i.e., the characteristic two clusters for erythroblasts, which stand in contrast to a single loosely distributed cluster for bacterial signals.

Although the apparatus and method described in U.S. Pat. Nos. 5,516,695 and 5,559,037 were originally designed to perform analysis of white blood cell differential and erythroblasts in blood samples simultaneously, it has been discovered that the same apparatus and method can also be utilized in analyzing particles even smaller than nuclei of erythroblasts, such as, for example, those containing the genetic material DNA or RNA, which are found in bacteria in body fluids, such as, for example, cerebrospinal fluid, pleural fluid, peritoneal fluid, pericardial fluid, synovial fluid, ascites fluid, drain fluid, and dialysate fluid. It is also contemplated that the method described herein can also be used to detect and count bacteria in blood, i.e., blood is deemed to be a member of the class of body fluids.

In another embodiment, samples of certain body fluids, such as, for example, synovial fluid, can be pretreated with a viscosity reducing agent, such as, for example, hyaluronidase, for a short period of time to reduce the viscosity of the sample of the body fluid prior to analyzing the sample by an automated hematology analyzer, such as the analyzer described in U.S. Pat. No. 5,939,326, incorporated herein by reference. To be qualified as a valid bacterial signal, the amplitude of the signal must be below the OR gate, ALL trigger, but above the AND gate, FL3 and IAS triggers; and the algorithm(s) of the system carries out the function of differentiating bacterial signals from signals generated by erythroblasts by the size of the ALL signals, the intensity of the FL3+ signals from bacteria, and the shape and the number of FL3 clusters, i.e., the characteristic two clusters for erythroblasts, which stand in contrast to a single loosely distributed cluster for bacterial signals.

Patterns for ALL, IAS, PSS, and FL3 signals and the location of bacterial signals are different from those of white blood cell subsets or erythroblasts. Accordingly, bacterial signals are easily identified by the algorithm(s) of the system by using appropriate logic for the sizes of the cells, fluorescence intensity, and the pattern and location of the clusters to differentiate bacterial signals from those of erythroblasts or white blood cells.

It is preferred that clusters of bacteria be clearly identifiable by both light scatter at specifically selected angles and fluorescence axis and that noise signals from debris be blocked by a triple-triggering circuitry that qualifies valid signals, such as those generated by white blood cells and erythroblasts, as described in U.S. Pat. No. 5,559,037, incorporated herein by reference. In addition, it is preferred that bacterial clusters be distinguishable from those of erythroblasts; otherwise, erythroblast nuclei would appear as bacteria and be counted as such, thereby yielding false positive results for bacteria. Software algorithm(s) for analyzing signals determine where each cluster lies and then determines where the bacterial cluster resides, and then counts the number of events accordingly. The signals from erythroblast nuclei always form two distinct clusters along the FL3 axis, one large and one small, whereas FL3 signals from bacteria always have higher FL3+ signal amplification than those from erythroblasts and form a loosely distributed single cluster, not two distinct clusters, which characterize the distribution of erythroblasts.

DETAILED DESCRIPTION

Figure 1:
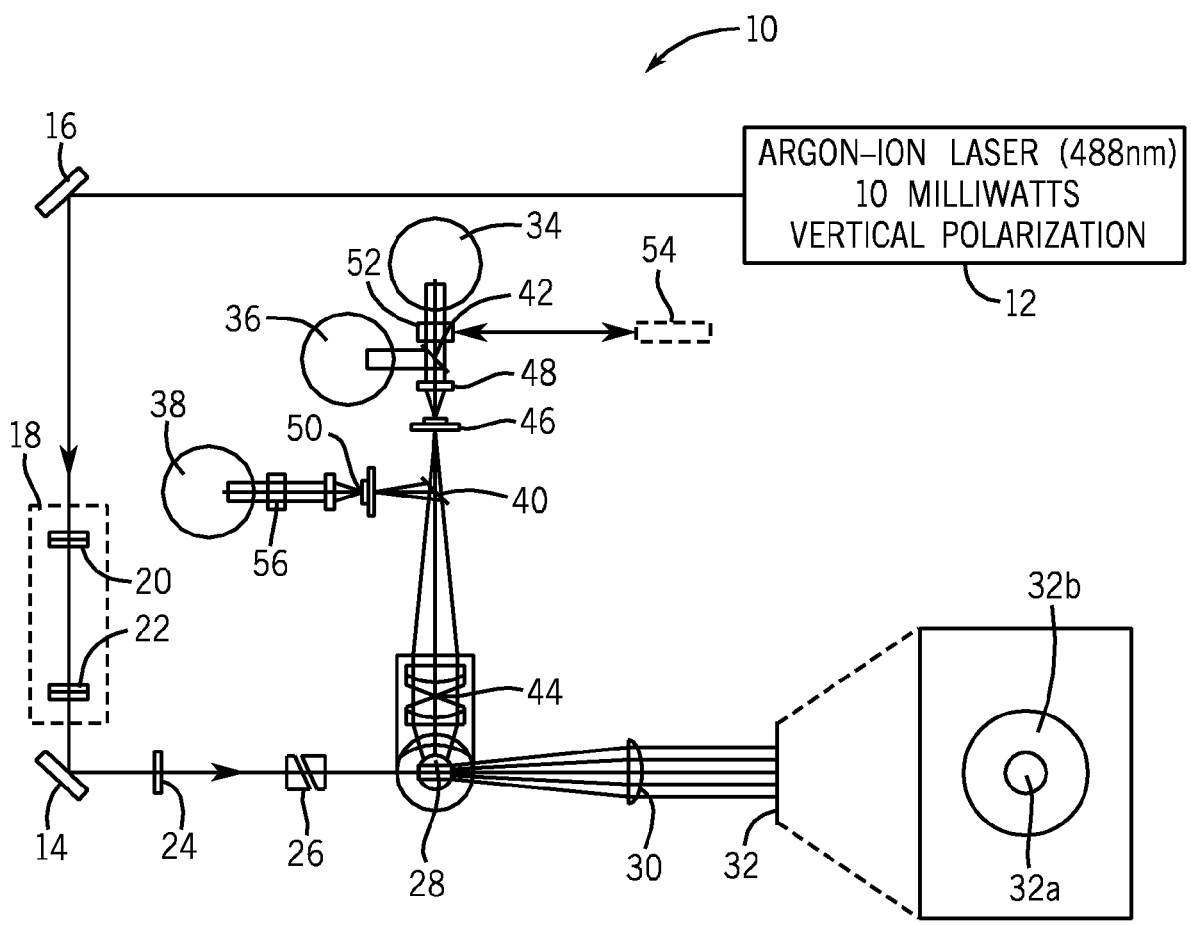
FIG. 1 is a schematic diagram illustrating the illumination and detection optics of an apparatus suitable for generating three-dimensional signals from white blood cells, erythroblasts, and bacteria for differential analysis.

As used herein the expression "axial light loss" and "ALL" refer to the measurement of the total light lost from the laser beam at from about 0° to about 1° when a particle passes through the beam. This parameter relates to measurement of the size of cells or particles passing through the optical detection system. As used herein, the expressions "intermediate angle scatter" and "IAS" refer to the measurement of forward light scatter at intermediate angle from 3° to 10°. This parameter relates to measurement of complexity of a cell. As used herein, the term "complexity" refers to the composition of a cell. Some cells have mitochondria, ribosomes, nucleus, while other cells lack one or more of the foregoing components. The measured intensity of IAS depends to some degree on the heterogeneity of the contents of a cell (or particle) passing through the illumination beam of a cytometer. The density of "IAS" signals can be thought of as a measure of the complexity of the contents of the cell, i.e., the presence of organelles, such as, for example, nuclei, vacuoles, endoplasmic reticula, mitochondria, etc. As used herein, the expressions "polarized side scatter" and "PSS" refer to polarized light scatter at the angle of 90°. This parameter relates to measurement of lobularity. The nuclei of cells have various shapes that may result in one to five lobules, inclusive. A representative example of a cell with multi-lobed nucleus is a segmented neutrophil. As used herein, the expressions "depolarized side scatter" and "DSS" refer to depolarized light scatter at the angle of 90°. This parameter relates to measurement of subpopulations of blood cells. Blood cells have various numbers of subpopulations within the membranes of the cell. Examples of these subpopulations, for white blood cells, are eosinophils, neutrophils, basophils, monocytes and lymphocytes. As used herein, the expression "FL1" refers to fluorescence measurement at an emission signal wavelength of 530 nanometers, i.e., green fluorescence. As used herein, the expression "FL2" refers to fluorescence measurement at an emission signal wavelength of 580 nanometers, i.e., yellow to orange fluorescence. As used herein, the expression "FL3" refers to fluorescence measurement at an emission signal wavelength of 630 nanometers, i.e., red fluorescence. This parameter relates to measurement of DNA or RNA stained by a nuclear stain used in the reagent system.

As used herein, the term "trigger" means the minimum electrical voltage that an electrical signal must exceed to be considered valid. As used herein, the expression "triple-trigger" refers to a circuitry processing signals based on AND/OR logic wherein a qualified signal must be greater than the second scatter signal threshold, while at the same time it must be greater than either the first scatter signal threshold or the FL3 threshold.

As used herein, the term "erythroblast" means any of the nucleated cells in bone marrow that develop into erythrocytes. As used herein, the term "erythrocyte" means the yellowish, non-nucleated, disk-shaped blood cell that contains hemoglobin and is responsible for the color of blood. As used herein, the expression "erythroblast nuclei" refers to the nuclei of erythroblasts.

One or more detectors are preferably placed in the light path for measuring forward intermediate angle scattering (IAS) and either small angle forward scattering (SAS) or axial light loss (ALL). The light loss is generally due to scattering and defined as the decrease in light energy reaching a detector in the path of a laser beam due to the passage of a cell through that beam. Generally ALL is detected at an angle of from about 0° to about 1°. SAS is light energy that reaches a detector outside, but within a narrow angle of about 1° to about 3°, the incident laser beam due to scattering from a cell passing through the beam. A beam stop is generally provided to keep the laser beam from getting into the detector. ALL measuring systems collect light within the incident cone of laser illumination, while small angle scatter systems collect light outside this cone. In ALL measuring systems, the signal of interest is a negative signal subtracted from the steady state laser signal, whereas in the small angle forward scatter measurement, the signal is a small positive signal imposed on a very low background light level. Intermediate angle forward scattering (IAS) is similar to small angle forward scattering, except the light is scattered at a larger angle from the incident laser beam. More specifically, IAS relates to light scattered in a ring between 3° and 10° away from the incident or centerline of a laser beam. In a preferred embodiment, ALL is collected in the angles less than 0.3° horizontally and less than 1.2° vertically from the laser axis, and IAS is collected at angles between 3° and 10° from the laser axis.

As used herein, the term "drain" means drainage, the systematic withdrawal of fluids and discharges from wound of body cavity.

As used herein, the expression "Open Mode" means that the sample is presented directly to the automated instrument by a human operator. As used herein, the expression "Closed Mode" means that the sample is presented directly to the automated instrument by a robotic mechanism.

As used herein, the expression "measuring cells" refers to enumerating cells by means of light scattering techniques to determine, size, granularity, lobularity, and fluorescence when the cells are stained with a particular dye of fluorochrome.

As used herein, the expression "cell surface antigen" means a substance that promotes the generation of antibodies. The cell surface antigens are endogenous antigens that have been generated within the cell, as a result of normal cell metabolism, or because of viral or intracellular bacterial infection. The fragments are then presented on the cell surface in the complex with MHC class I molecules.

The expression "red blood cell ghost" refers to the red blood cell membrane remaining after a red blood cell is lysed either by hypotonic medium or by a lysing reagent.

The symbol "(s)" following the name of an object indicates that either the object alone or a plurality of the objects is being referred to, depending upon the context of the statement surrounding the mention of the object or objects.

Automated hematology analyzers are discussed in WHITNEY WILLIAMS. Hem I Automated Cell Counting and Evaluation. Educational publication [online], [retrieved on 2008-07-15]. Retrieved from the Internet: <URL: http://www.clt.astate.edu/wwilliams/new_page_4.html>, incorporated herein by reference.

The method described herein involves an automated method for simultaneous analysis of white blood cell differential, erythroblasts, and bacteria in body fluids, such as, for example, blood, cerebrospinal fluid, ascites fluid, pleural fluid, peritoneal fluid, pericardial fluid, synovial fluid, dialysate fluid, and drain fluid, on a hematology analyzer by means of the same reagent system and optical detection system designed for analysis of blood.

Referring now to FIG. 1, an apparatus 10 comprises a source of light 12, a front mirror 14 and a rear mirror 16 for beam bending, a beam expander module 18 containing a first cylindrical lens 20 and a second cylindrical lens 22, a focusing lens 24, a fine beam adjuster 26, a flow cell 28, a forward scatter lens 30, a bulls-eye detector 32, a first photomultiplier tube 34, a second photomultiplier tube 36, and a third photomultiplier tube 38. The bullseye detector 32 has an inner detector 32a for 0° light scatter and an outer detector 32b for 7° light scatter.

The source of light 12 can be a vertically polarized 488 nm air-cooled argon-ion laser or a linearly polarized blue (488 nm) diode-pumped solid-state (DPSS) laser. Additional details relating to the laser, the flow cell, the lenses, the focusing lens, the fine-beam adjust mechanism and the laser focusing lens can be found in U.S. Pat. No. 5,631,165, incorporated herein by reference, particularly at column 41, line 32 through column 43, line 11.

The preferred forward optical path system shown in FIG. 1 includes a spherical plano-convex lens 30 and a two-element photo-diode detector 32 located in the back focal plane of the lens. In this configuration, each point within the two-element photodiode detector 32 maps to a specific collection angle of light from cells moving through the flow cell 28. The detector 32 can be a bulls-eye detector capable of detecting axial light loss (ALL) and intermediate angle forward scatter (IAS). U.S. Pat. No. 5,631,165 describes various alternatives to this detector at column 43, lines 12-52.

The first photomultiplier tube 34 (PMT1) measures depolarized side scatter (DSS) or green fluorescence (FL1). The second photomultiplier tube 36 (PMT2) measures polarized side scatter (PSS) or yellow to orange fluorescence (FL2) and the third photomultiplier tube 38 (PMT3) measures red fluorescence (FL3). FL1, green fluorescence, is detected between about 515 to 545 nm. FL2, yellow to orange fluorescence, is detected between about 565 to 595 nm. FL3, red fluorescence, is detected between about 615 to 645 nm. Side-scatter and fluorescent emissions are directed to these photomultiplier tubes by dichroic beam splitters 40 and 42, which transmit and reflect efficiently at the required wavelengths to enable efficient detection. U.S. Pat. No. 5,631,165 describes various additional details relating to the photomultiplier tubes at column 43, line 53 though column 44, line 4.

Sensitivity is enhanced at photomultiplier tubes 34, 36, and 38, when measuring fluorescence, by using an immersion collection system. The immersion collection system is one that optically couples the first lens 30 to the flow cell 28 by means of a refractive index matching layer, enabling collection of light over a wide angle. U.S. Pat. No. 5,631,165 describes various additional details of this optical system at column 44, lines 5-31.

The condenser 44 is an optical lens system with aberration correction sufficient for diffraction limited imaging used in high resolution microscopy. U.S. Pat. No. 5,631,165 describes various additional details of this optical system at column 44, lines 32-60.

The functions of other components shown in FIG. 1, i.e., a slit 46, a field lens 48, and a second slit 50, are described in U.S. Pat. No. 5,631,165, at column 44, line 63 through column 45, line 15. The photomultiplier tubes 34, 36, and 38 detect either side-scatter (light scattered in a cone whose axis is approximately perpendicular to the incident laser beam) or fluorescence (light emitted from the cells at a different wavelength from that of the incident laser beam). A movable polarizer 52 placed in the light path of the photomultiplier tube 34 configures the photomultiplier tube 34 to detect depolarized side-scatter (DSS) and polarized side-scatter (PSS), respectively, while movable filters 54, 56, 58 enable detection of fluorescent emissions at specified wavelengths from the cells.

The measurement process begins as the cell stream passes through the flow cell 28, having been diluted with the lysing agent so that the cells pass through the laser illuminated volume single file, in a laminar flowing sample stream surrounded by a sheath solution. The illuminated volume is bounded in the two directions normal to the flow axis by the hydrodynamically focused cell stream, and in the dimension parallel to the flow axis by the vertical beam waist of the laser beam, which is about 17 micrometers. The flow rate of the sample is about 2.5 microliters per second, and the corresponding illuminated sensing volume of the white blood cells and the erythroblasts approximates an elliptical cylinder having dimensions of about 80 µm×5 µm×17 µm. The 17 µm dimension is measured along the axis of the elliptical cylinder.

The presence of a cell in the illuminated region is detected by the photodiodes and the photomultiplier tubes, and a triple threshold trigger circuit that operates in three feature space dimensions. That is, the triple threshold trigger circuit processes the three parameters of ALL, IAS, and FL3 and qualifies signals for digitization using AND/OR logic. A qualified signal must be greater than the IAS threshold while at the same time it must be greater than either the ALL threshold or the FL3 threshold. The combination of this triggering circuit and the lysing properties (which lightly fixes white blood cells and preserves their surface antigens while at the same time permitting erythrocyte nuclei to be rapidly stained) excludes erythroblasts from the white blood cell differential count. Bacterial signals are distinguished from those of erythroblasts by the size, shape, and the location of the distribution of the respective signals by the algorithm(s) of the system. The method described herein counts white blood cell populations, erythroblasts, and bacteria without the interference typically encountered from background signals, both fluorescent and non-fluorescent, red blood cell stroma, and platelets. U.S. Pat. No. 5,631,165 describes various additional details of the measurement process at column 55, line 48 through column 59, line 43.

Figure 2:
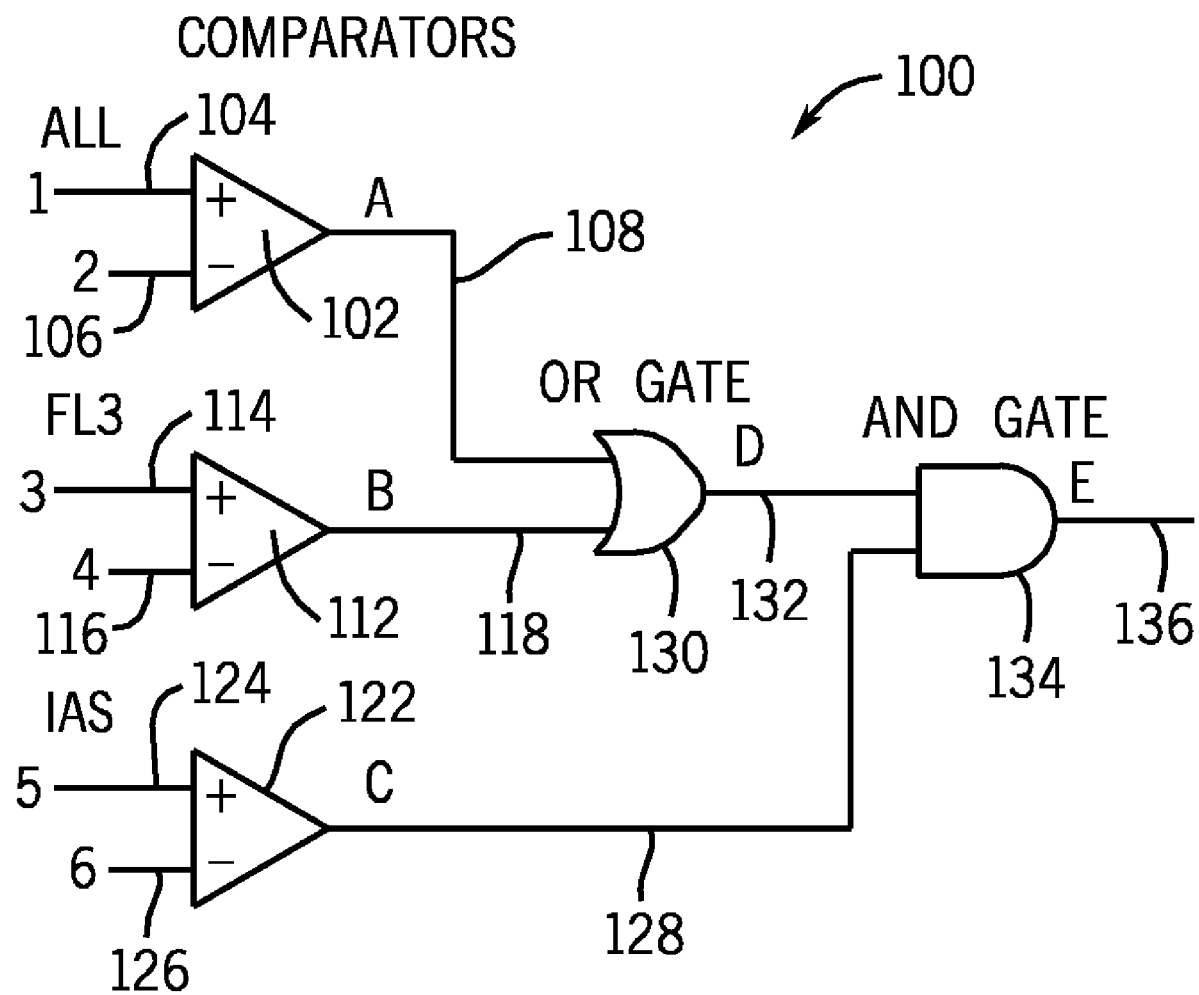
FIG. 2 is a block diagram illustrating the triple-trigger circuitry suitable for use in the apparatus described herein. This circuitry eliminates signals from debris and qualifies signals form white blood cells, erythroblast nuclei, and bacteria.

Referring now to FIG. 2, (AND/OR) circuitry eliminates signals from debris and qualifies signals from erythroblast nuclei or bacteria in addition to those of white blood cells. To be qualified as a valid signal, a signal must be either above ALL OR FL3 trigger and always above AND GATE, which is IAS AND FL3. The electrical pulse mechanism will perform three distinct measurements. First, positive or negative measurements of ALL are carried out. Then positive or negative measurements of FL3 are carried out. Finally, positive or negative measurements of IAS are carried out. By separating positive and negative pulses, the triple triggering circuitry utilizes the gating mechanism to differentiate white blood cells from erythroblasts. The final gating mechanism further separates and identifies the smallest of the particles, such as, for example, platelets. The bacterial signals (FL3+) will be qualified by the circuitry along with the signals generated by erythroblasts because the amplification of FL3+ bacterial signals is above the FL3 threshold. Bacterial signals are differentiated from those of erythroblasts by the software algorithm, because the amplification of ALL signals from bacteria is lower and the intensity of FL3 signals from bacteria is higher than those generated by erythroblasts. All signals exceeding a minimum voltage are used, because these signals are deemed to be valid. The components of the AND/OR circuitry 100 are as follows:

102 ALL Voltage Comparator
    104 ALL Signal
    106 ALL threshold voltage (Vth1)
    108 ALL Voltage Comparator Output
    112 FL3 Voltage Comparator
    114 FL3 Signal
    116 FL3 threshold voltage (Vth2)
    118 FL3 Voltage Comparator Output
    122 IAS Voltage Comparator

124 IAS Signal
126 IAS threshold voltage (Vth3)
128 IAS Voltage Comparator Output
130 OR Gate
132 OR Gate output
134 AND Gate
136 Valid Trigger Output Real time signals from their respective channels are present at the inputs of the voltage comparators. Voltage comparators 102, 112, 122 function by comparing the "+inputs" 104, 114, 124 to the "−inputs" 106, 116, 126 to resultant outputs 108, 118, 128. If the "+input" is of a higher voltage than the "−input", the output will be high. If the "+input" is of a lower voltage than the "−input", the output will be low.

The threshold voltages are independent voltages that are determined by parameters of the system. The outputs of comparators 102 and 112 are inputs to OR gate 130 to give resultant OR gate output 132. The OR gate functions by comparing its inputs. The output will be high if either, or both, inputs are high.

The output 132 of the OR gate 130 and the output of comparator 122 are inputs to AND gate 134. The AND gate functions by comparing its inputs to derive its output 136 which is also the valid trigger output. The output will be high only if both inputs are high.

The valid trigger output 136 will be high only if the IAS signal 124 is greater than its threshold voltage 126, and if the ALL signal 104 is greater than its threshold voltage 106 or the FL3 signal 114 is greater than its threshold voltage 116, or both the ALL signal 104 is greater than its threshold voltage 106 and the FL3 signal 114 is greater than its threshold voltage 116.

In one embodiment, a body fluid can be analyzed without any manual preparation on the system in the Open Mode feature. A portion of the sample of the body fluid can be diluted with a diluent to enable a minimal number of cells to pass through a counting aperture at the same time. The diluent is typically used for the channel that counts red blood cells. A sample of the body fluid is mixed with a reagent system that was originally designed to preserve white blood cells and their cell surface antigens for immuno-phenotyping, i.e., a technique used for analyzing and measuring cells labeled with specific monoclonal antibodies conjugated to specific fluorochromes to locate specific cell surface antigens, and at the same time red blood cells and membranes of erythroblasts are lysed and nuclei of erythroblasts and bacterial DNA or RNA are stained. Then, the cells that were treated with the aforementioned reagent system are passed through the electro-optical system described in FIG. 1 in single file and the electronic logic, triple-triggering circuitry of the system, and the algorithm(s) of the system differentiate each cell population based on cell volume, i.e., size of the cells, complexity of the cells, lobularity of the cells, refractive index of the cells, fluorescence intensity, and the location and pattern of each cell cluster. The triple-triggering circuitry eliminates signals from cell debris and qualifies signals from white blood cells, erythroblasts, and bacteria. Signals that are eliminated have values below a specified cut-off, and the eliminated signals are deemed debris. Signals that are qualified have values above a specified cut-off, and the qualified signals are deemed white blood cells, erythroblasts, and bacteria. To be qualified as valid bacterial signals, the amplitude of the signals must be below the OR Gate, ALL trigger, but above the AND Gate, FL3 and IAS triggers. The software algorithm(s) of the system can be used to differentiate bacterial signals from that of erythroblasts signals by the size of the ALL signal, the intensity of the FL3+ signals from bacteria, and the shape and the number of FL3 clusters, i.e., the characteristic two clusters for erythroblasts, which stand in contrast to a single loosely distributed cluster for bacterial signals.

The first logic analysis is of the complete system and all of its attributes. The second logic analysis is a derivative of the logic analysis of the complete system and relates to the distinction between erythroblasts and bacteria. Amplification of ALL signals from bacteria is lower than amplification of ALL signals from erythroblasts; accordingly, ALL signals from bacteria fall below clusters of erythroblast signals. Furthermore, clusters of erythroblasts always appear as two distinct clusters, in contrast to the single loosely distributed cluster of bacterial signals. Still further, amplification of FL3+ signals from bacteria is much higher than amplification of FL3+ signals from erythroblasts.

The following non-limiting examples further illustrate the method described herein. In the drawings, the letter "N" indicates the position of neutrophils in the cytograms, the letter "M" indicates the position of monocytes in the cytograms, the letter "L" indicates the position of lymphocytes in the cytograms, the letter "E" indicates the position of eosinophils in the cytograms, the letter "B" indicates the position of basophils in the cytograms, the letter "P" (or the letter "P" preceded by a numeral) indicates the position of platelets in the cytograms, and the letter "X" (or the letter "X" preceded by a numeral) indicates the position of bacteria in the cytograms. The terms "Erb1", "Erb2", and "Erb 1+2" indicate the positions of a first cluster of erythroblasts, a second cluster of erythroblasts, and a cluster combining the two clusters of erythroblasts, respectively.

EXAMPLES

Comparative Examples A, B, and C illustrate how cytograms resulting from the method described herein characterize white blood cells in an automated hematology analyzer described in U.S. Pat. Nos. 5,631,165; 5,656,499; and 5,939,326. Working Examples 1, 2, 3, 4, and 5 illustrate how cytograms resulting from the method described herein differentiate bacteria from white blood cells and count bacterial cells in an automated hematology analyzer described in U.S. Pat. Nos. 5,631,165; 5,656,499; and 5,939,326.

Comparative Example A

Referring now to FIGS. 3A, 3B, 3C, and 3D, a sample of normal blood was treated with the reagent system described in U.S. Pat. Nos. 5,516,695 and 5,559,037, both of which were previously incorporated herein as reference. This reagent system was also used in Comparative Examples B and C and Working Examples 1, 2, 3, 4, and 5. The reagent system comprises a red blood cell lysing component, a white blood cell preserving component, and a nuclear stain. The apparatus of FIGS. 1 and 2 can be used to prepare a cytogram of a blood sample of a patient. The sample contained white blood cells at a concentration of $6.08 \times 10^3/\mu L$, lymphocytes (35.1%), neutrophils (54.5%), monocytes (6.95%), eosinophils (3.34%) and basophils (0.07%).

Figure 3A:
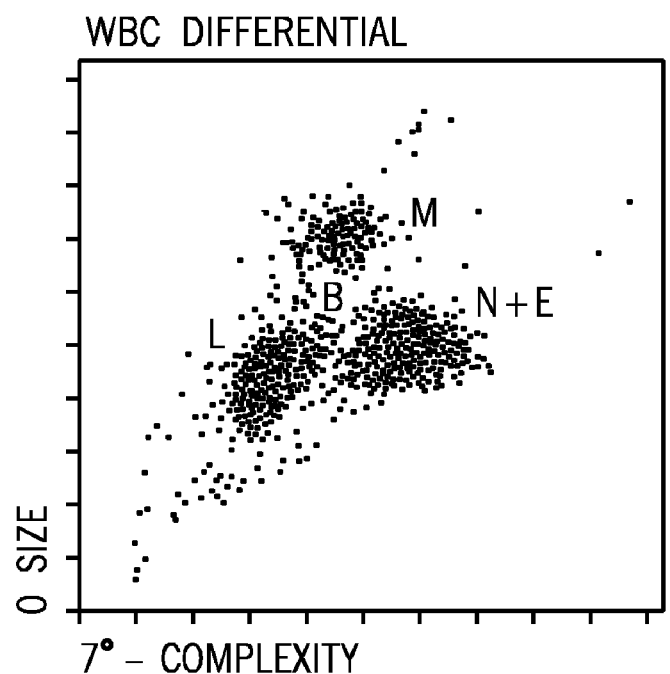
FIG. 3A is a cytogram of the white blood cells of a sample of normal blood, wherein the X-axis corresponds to intermediate angle light scatter (IAS) signals from 3° to 10°, and the Y-axis corresponds to axial light loss (ALL) signals, as measured by the apparatus depicted in FIGS. 1 and 2.
Figure 3B:
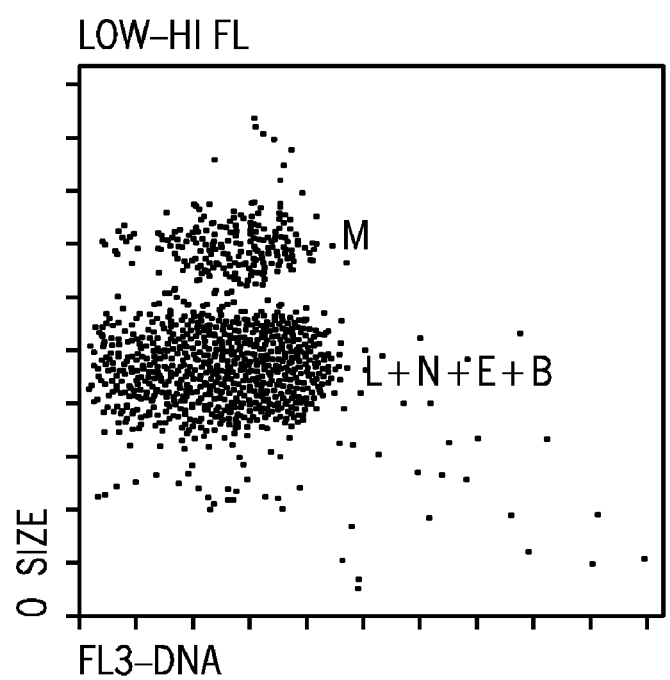
FIG. 3B is a cytogram of the white blood cells of a sample of the same blood as in FIG. 3A, except that the X-axis corresponds to red fluorescent (FL3) signals, and the Y-axis corresponds to ALL signals, as measured by the apparatus depicted in FIGS. 1 and 2.

Red blood cell (RBC) indices were analyzed with the same reagent system by means of an impedance measurement. FIG. 3A is a cytogram of the white blood cells of a sample of normal blood, wherein the X-axis corresponds to intermediate angle light scatter (IAS) signals from 3° to 10°, and the Y-axis corresponds to axial light loss (ALL) signals, as measured by the apparatus depicted in FIGS. 1 and 2. FIG. 3B is a cytogram of the white blood cells of a sample of the same blood as in FIG. 3A, except that the X-axis corresponds to red fluorescent (FL3) signals, and the Y-axis corresponds to ALL signals, as measured by the apparatus depicted in FIGS. 1 and 2. As can be seen in FIG. 3B, the area above the FL3 trigger, originally designated for detection of erythrocytes, is clear, thereby indicating that no erythrocytes were found in the sample.

Figure 3C:
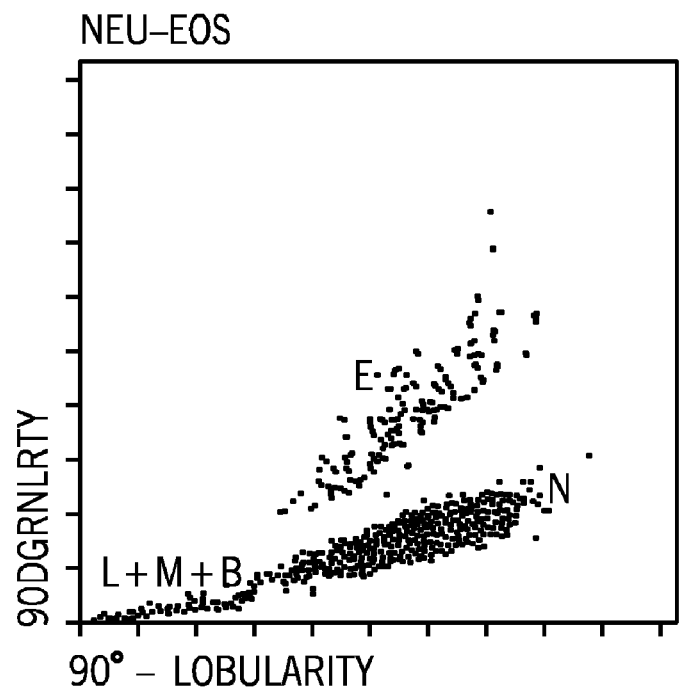
FIG. 3C is a cytogram of the white blood cells of a sample of the same blood as in FIG. 3A, except that the X-axis corresponds to 90° polarized side scatter (PSS) signals and the Y-axis corresponds to 90° depolarized side scatter (DSS) signals, as measured by the apparatus depicted in FIGS. 1 and 2.

FIG. 3C is a cytogram of the white blood cells of a sample of the same blood as in FIG. 3A, except that the X-axis corresponds to 90° polarized side scatter (PSS) signals and the Y-axis corresponds to 90° depolarized side scatter (DSS) signals, as measured by the apparatus depicted in FIGS. 1 and 2. The amplification of DSS signals from eosinophils is much higher than those from all other white blood cells. Thus, eosinophils are separated from the rest of the white blood cells by the algorithm(s) of the system and counted. Eosinophils are highly granulated.

Figure 3D:
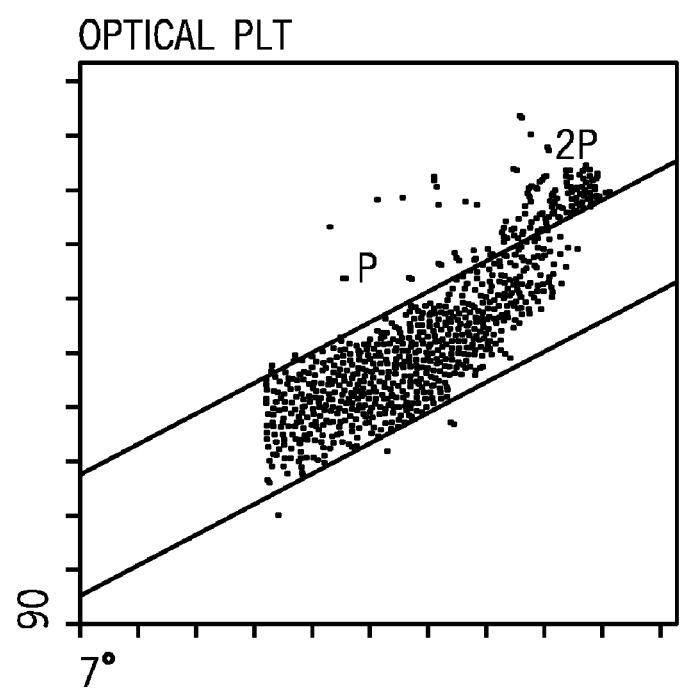
FIG. 3D is a cytogram of a sample of the same blood as in FIG. 3A, except that the scatter signals in this cytogram are from a different electronic scale, which uses much higher electronic gains, and is designed to measure platelets. A cytogram of the platelet (PLT) channel is included because light scatter signals from bacteria also appear in this cytogram, thereby providing a cross-check capability for the presence of bacteria in the sample. The X-axis corresponds to IAS signals and the Y-axis corresponds to PSS signals, as measured by the apparatus depicted in FIGS. 1 and 2.

FIG. 3D is a cytogram of a sample of the same blood as in FIG. 3A, except that the scatter signals in this cytogram are from a different electronic scale, which uses much higher electronic gains, and is designed to measure platelets. In FIG. 3D, it can be seen that the background outside the platelet population enclosed by the two floating threshold lines generated by the platelet algorithm of the system is clean. The two parallel lines that appear on the cytogram in FIG. 3D, and the cytograms in FIGS. 4D, 6D, 7D, 8D, 9D, and 10D, represent the two floating thresholds. The X-axis corresponds to IAS signals and the Y-axis corresponds to PSS signals, as measured by the apparatus depicted in FIGS. 1 and 2.

Comparative Example B

The same method and apparatus that were used in COMPARATIVE EXAMPLE A were used to carry out COMPARATIVE EXAMPLE B.

Figure 4A:
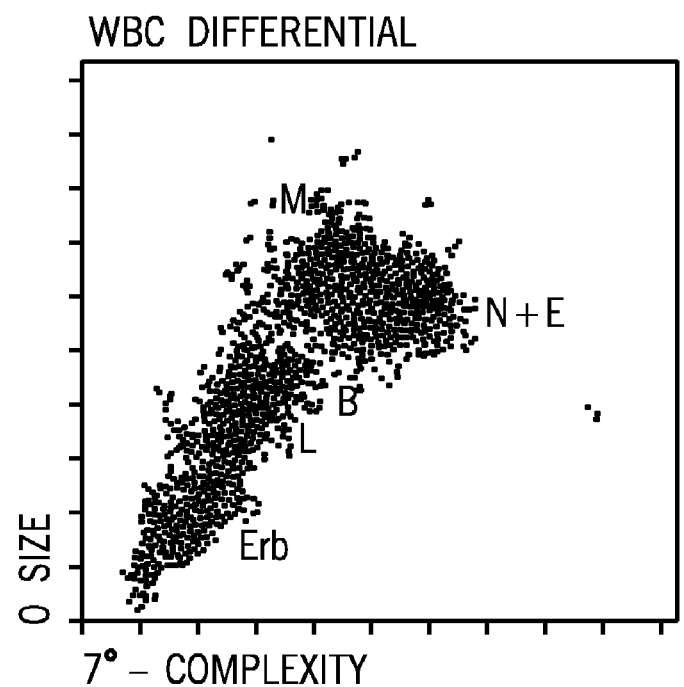
FIG. 4A is a cytogram of the white blood cells of a clinical blood sample containing erythroblasts, wherein the X-axis corresponds to IAS signals and the Y-axis corresponds to ALL signals, as measured by the apparatus depicted in FIGS. 1 and 2.

FIG. 4A is a cytogram of the white blood cells of a clinical blood sample containing erythroblasts, wherein the X-axis corresponds to IAS signals and the Y-axis corresponds to ALL signals, as measured by the apparatus depicted in FIGS. 1 and 2. The concentration of white blood cells was $20.9 \times 10^3/\mu L$, and the concentration of erythroblasts was $2.38 \times 10^3/\mu L$. Unlike FIG. 3A, very high noise-like signals appear below the lymphocyte cluster in FIG. 4A.

Figure 4B:
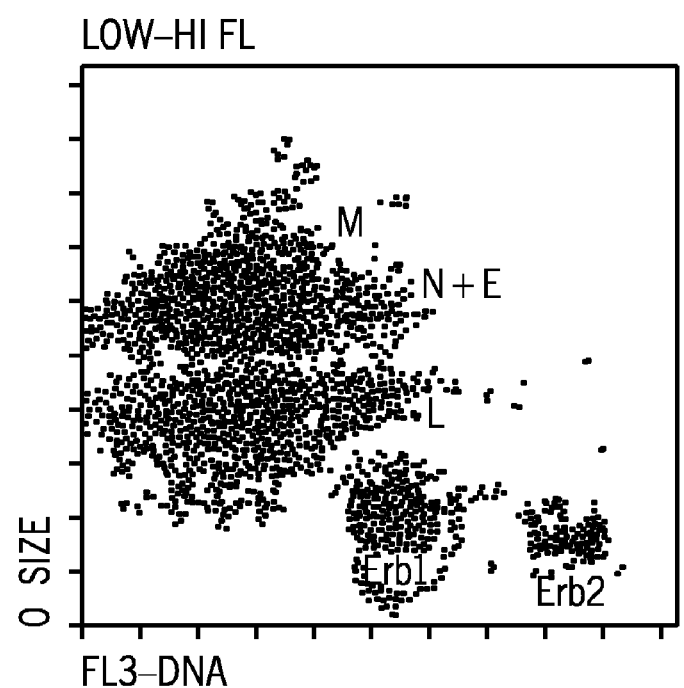
FIG. 4B is a cytogram of the white blood cells of a clinical sample of the same blood as in FIG. 4A, except that the X-axis corresponds to FL3 signals and the Y-axis corresponds to ALL signals, as measured by the apparatus depicted in FIGS. 1 and 2.

FIG. 4B is a cytogram of the white blood cells of a clinical sample of the same blood as in FIG. 4A, except that the X-axis corresponds to FL3 signals and the Y-axis corresponds to ALL signals, as measured by the apparatus depicted in FIGS. 1 and 2. In FIG. 4B, the area below the ALL trigger but above the FL3 trigger is occupied by the characteristic pair of FL3+ erythroblasts, one larger primary cluster centered around the channel 125 of the X-axis and a second smaller cluster centered around the channel 220 of the X-axis. It should be noted that the X-axis has 256 channels, running from a value of 0 to a value of 256. Because the size of erythroblast nuclei is much smaller than that of white blood cells, the ALL signals of erythroblast nuclei fall below the ALL trigger. The heavy noise-like signals appearing below the lymphocyte cluster in FIG. 4A also belong to the erythroblast population.

Figure 4C:
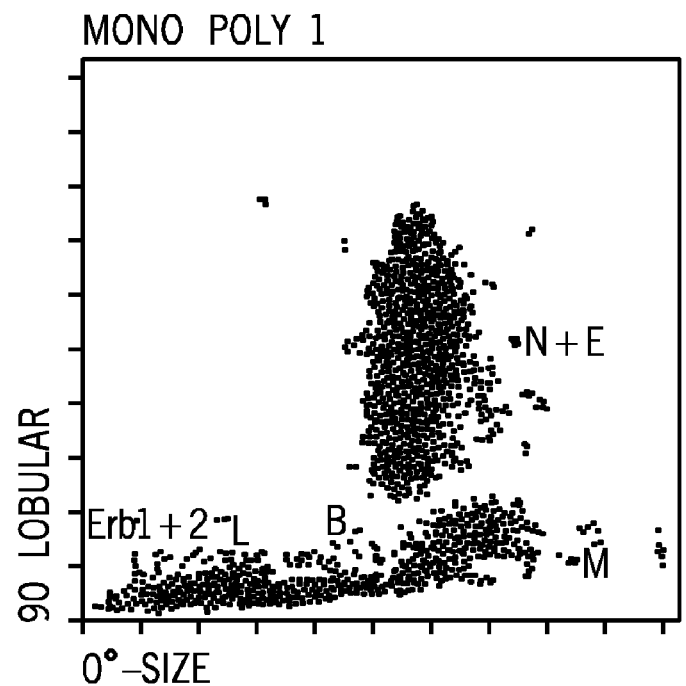
FIG. 4C is a cytogram of the white blood cells of a clinical sample of the same blood as in FIG. 4A, except that the X-axis corresponds to ALL signals and the Y-axis corresponds to PSS signals, as measured by the apparatus depicted in FIGS. 1 and 2.

FIG. 4C is a cytogram of the white blood cells of a clinical sample of the same blood as in FIG. 4A, except that the X-axis corresponds to ALL signals and the Y-axis corresponds to PSS signals, as measured by the apparatus depicted in FIGS. 1 and 2. Granulocytes (neutrophils and eosinophils) generate much larger PSS signals on account of their morphological complexity than do mononuclear cells (lymphocytes and monocytes) or basophils, thereby permitting the algorithm(s) of the system to separate the granulocyte population from the rest of the white cell population along the Y-axis.

Figure 4D:
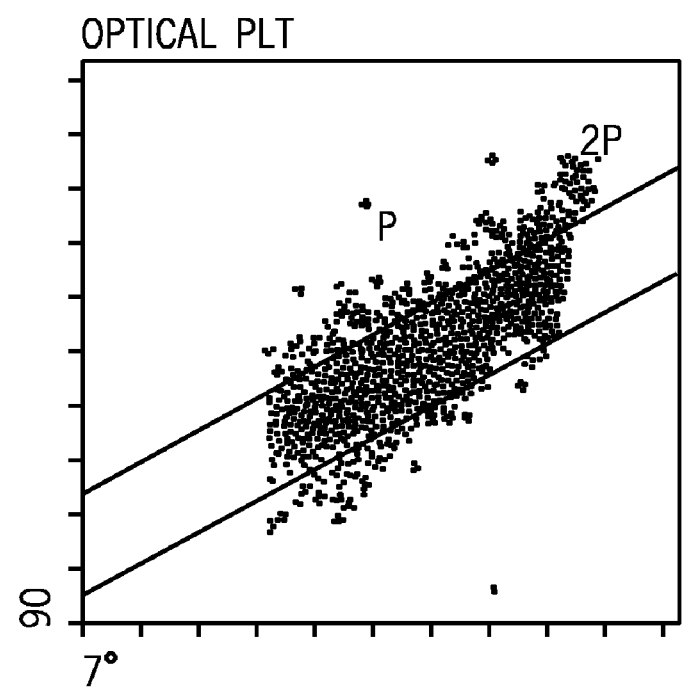
FIG. 4D is a cytogram of a clinical sample of the same blood as in FIG. 4A, except that the signals are from the PLT channel. The X-axis corresponds to IAS signals and Y-axis corresponds to PSS signals, as measured by the apparatus depicted in FIGS. 1 and 2.

FIG. 4D is a cytogram of a clinical sample of the same blood as in FIG. 4A, except that the signals are from the PLT channel. The X-axis corresponds to IAS signals and Y-axis corresponds to PSS signals, as measured by the apparatus depicted in FIGS. 1 and 2. In the platelet channel, the electronic gains of both scatter signals, PSS and IAS, are set much higher in order to amplify the signals generated by small platelets.

Comparative Example C

The same method and apparatus that were used in COMPARATIVE EXAMPLE A were used to carry out COMPARATIVE EXAMPLE C.

Figure 5A:
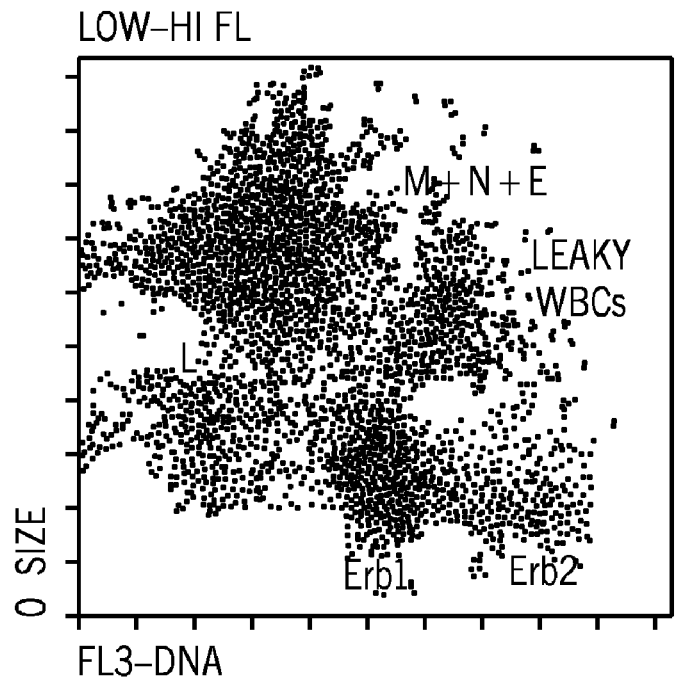
FIG. 5A is a cytogram of white blood cells of a clinical blood sample containing a very high concentration of erythroblasts, wherein the X-axis corresponds to FL3 signals and the Y-axis corresponds to ALL signals, as measured by the apparatus depicted in FIGS. 1 and 2.

FIG. 5A is a cytogram of a clinical blood sample containing very high concentration of erythroblasts, wherein the X-axis corresponds to FL3 signals and the Y-axis corresponds to ALL signals, as measured by the apparatus depicted in FIGS. 1 and 2. The concentration of erythroblasts is $4.93 \times 10^3/\mu L$. The pattern and the location of FL3+ erythroblast nuclei appear as two clearly visible clusters of erythroblasts, one large cluster and one small cluster. The concentration of white blood cells is $27.5 \times 10^3/\mu L$, neutrophils (86.6%), lymphocytes (7.96%), monocytes (4.49%), and eosinphils (0.84%). The primary cluster of erythroblasts is centered around the channel 127 of the X-axis, and the secondary cluster of erythroblasts is centered around the channel 220 of the X-axis.

Figure 5B:
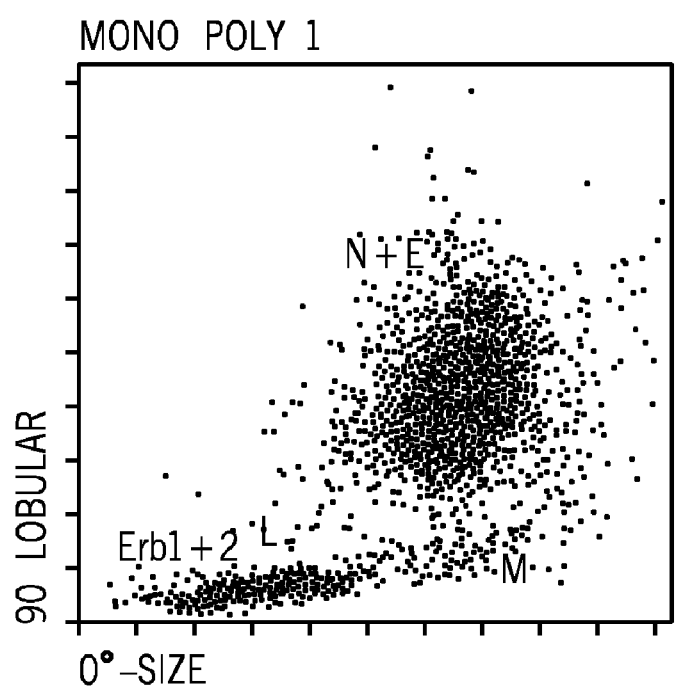
FIG. 5B is a cytogram of the same blood as in FIG. 5A, except that the X-axis corresponds to ALL signals and the Y-axis corresponds to PSS signals.

FIG. 5B is the same blood as in 5A, except that the X-axis corresponds to ALL signals and the Y-axis corresponds to PSS signals. As can be seen in FIG. 5B, no noticeable amount of PSS signals is generated from the very small particles located in the noise region below ALL trigger.

Example 1

The same method and apparatus that were used in COMPARATIVE EXAMPLE A were used to carry out EXAMPLE 1.

Figure 6A:
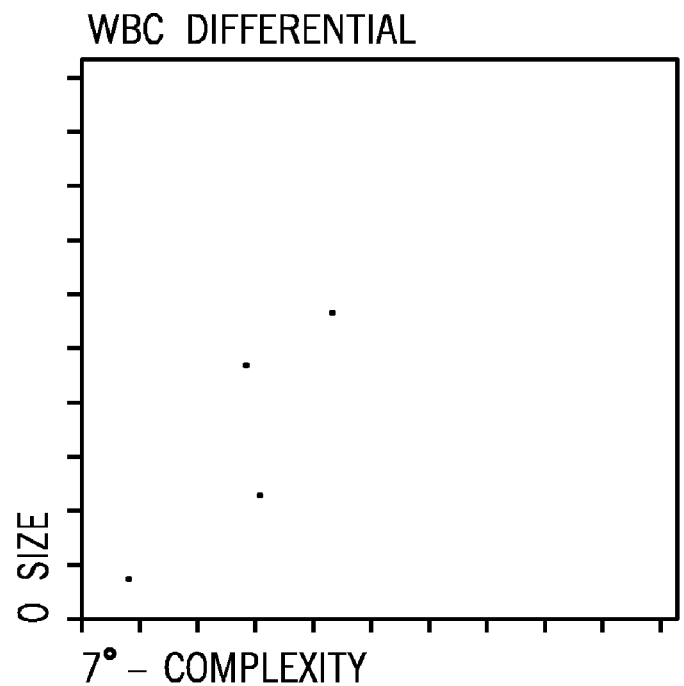
FIG. 6A is a cytogram of a clinical sample of cerebrospinal fluid (CSF), not suspected of carrying any infection, wherein the X-axis corresponds to IAS signals and the Y-axis corresponds to ALL signals, as measured by the apparatus depicted in FIGS. 1 and 2.
Figure 6B:
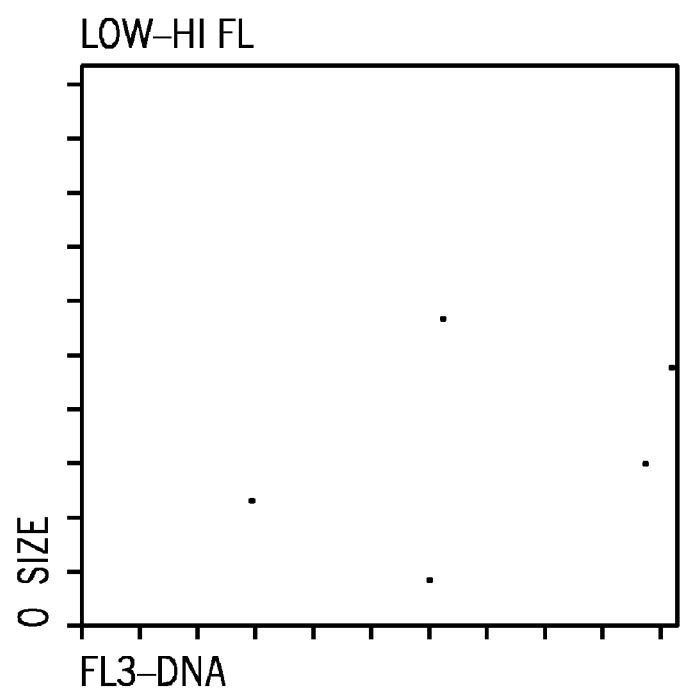
FIG. 6B is a cytogram of a clinical sample of the same CSF as in FIG. 6A, except that the X-axis corresponds to FL3 signals and the Y-axis corresponds to ALL signals, as measured by the apparatus depicted in FIGS. 1 and 2.
Figure 6C:
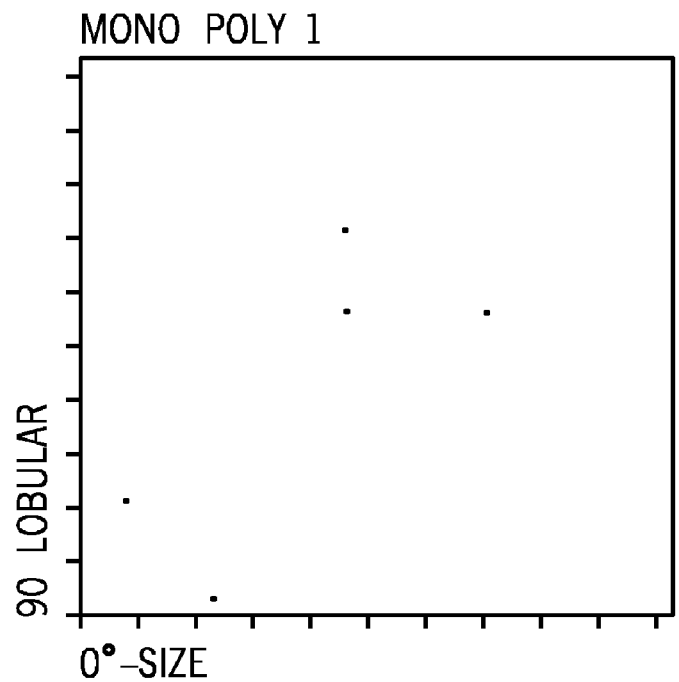
FIG. 6C is a cytogram of a clinical sample of the same CSF as in FIG. 6A, except that the X-axis corresponds to ALL signals and the Y-axis corresponds to PSS signals, as measured by the apparatus depicted in FIGS. 1 and 2.
Figure 6D:
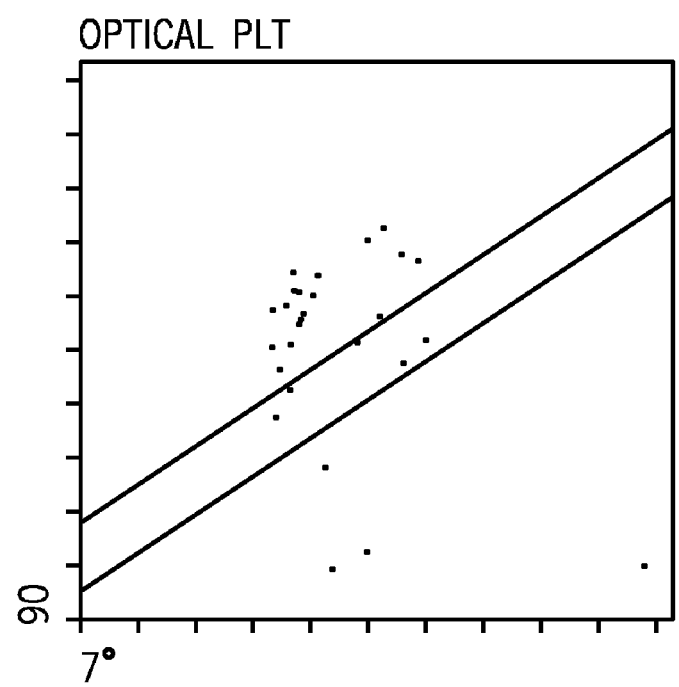
FIG. 6D is a cytogram of a clinical sample of the same CSF as in FIG. 6A, except that the signals are from the PLT channel, wherein the X-axis corresponds to IAS signals and the Y-axis corresponds to PSS signals, as measured by the apparatus depicted in FIGS. 1 and 2.

FIG. 6A is a cytogram of a clinical sample of cerebrospinal fluid (CSF), not suspected of carrying any infection, wherein the X-axis corresponds to IAS signals and the Y-axis corresponds to ALL signals, as measured by the apparatus depicted in FIGS. 1 and 2. FIG. 6B is a cytogram of a clinical sample of the same CSF as in FIG. 6A, except that the X-axis corresponds to FL3 signals and the Y-axis corresponds to ALL signals, as measured by the same apparatus depicted in FIGS. 1 and 2. FIG. 6C is a cytogram of a clinical sample of the same CSF as in FIG. 6A, except that the X-axis corresponds to ALL signals and the Y-axis corresponds to PSS signals, as measured by the apparatus depicted in FIGS. 1 and 2. FIG. 6D is a cytogram of a clinical sample of the same CSF as in FIG. 6A, except that the signals are from the PLT channel, wherein the X-axis corresponds to IAS signals and the Y-axis corresponds to PSS signals, as measured by the apparatus depicted in FIGS. 1 and 2. All the regions, ALL, IAS, PSS and FL3, for white blood cells and erythroblasts are clear, indicating that no cells are found in the specimen. The cytogram in FIG. 6D of the optical platelet channel is also clear, confirming that there are no small particles, such as bacteria in this sample of CSF.

Example 2

The same method and apparatus that were used in COMPARATIVE EXAMPLE A were used to carry out EXAMPLE 2.

Figure 7A:
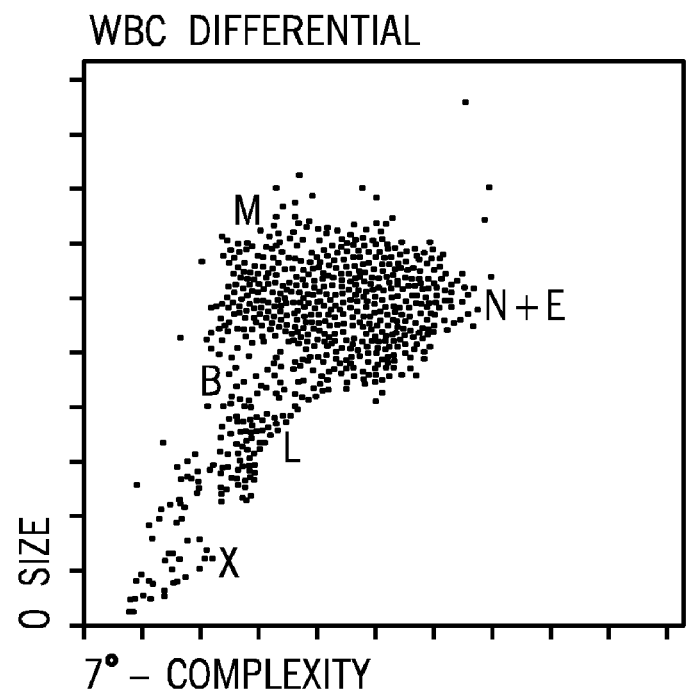
FIG. 7A is a cytogram of a clinical sample of CSF from a patient having a diagnosis of meningococcal sepsis. The X-axis corresponds to IAS signals and the Y-axis corresponds to ALL signals, as measured by the apparatus depicted in FIGS. 1 and 2.

FIG. 7A is a cytogram of a clinical sample of CSF from a 56-year old female patient having a diagnosis of meningococcal sepsis. The X-axis corresponds to IAS signals and the Y-axis corresponds to ALL signals, as measured by the apparatus depicted in FIGS. 1 and 2.

The sample contains white blood cells at a concentration of $5.06 \times 10^3/\mu L$, red blood cells at a concentration of $0.003 \times 10^6/\mu L$, neutrophils (86.8%), lymphocytes (5.4%), and monocytes (5.4%).

Figure 7B:
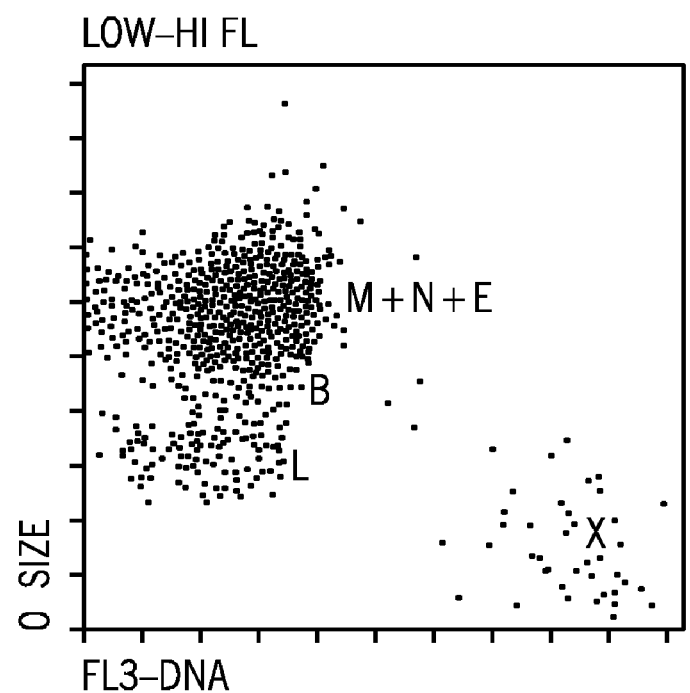
FIG. 7B is a cytogram of a clinical sample from the same CSF as in FIG. 7A, except that the X-axis corresponds to FL3 signals and the Y-axis corresponds to ALL signals, as measured by the apparatus depicted in FIGS. 1 and 2.

FIG. 7B is a cytogram of a clinical sample from the same CSF as in FIG. 7A, except that the X-axis corresponds to FL3 signals and the Y-axis corresponds to ALL signals, as measured by the apparatus depicted in FIGS. 1 and 2. The points in the circle below ALL channel 25 at far right corner of the cytogram in FIG. 7B correspond to bacterial cells, whose DNA is brightly stained by the reagent system, described in U.S. Pat. Nos. 5,516,695 and 5,559,037, both of which were previously incorporated herein by reference. The signal pattern and the location of the dots from the bacteria are distinguishable from those of erythroblasts in that the bacterial signals do not exhibit the characteristic primary and secondary pair of clusters of erythroblasts as seen in FIGS. 4B and 5A. Furthermore, the cell volume of bacteria is smaller than the cell volume of erythroblasts, with the result that ALL signals from bacteria fall below erythroblast signals centered around points along the X-axis, and the intensity of bacterial DNA staining is much brighter than that of erythroblast nuclei.

Figure 7C:
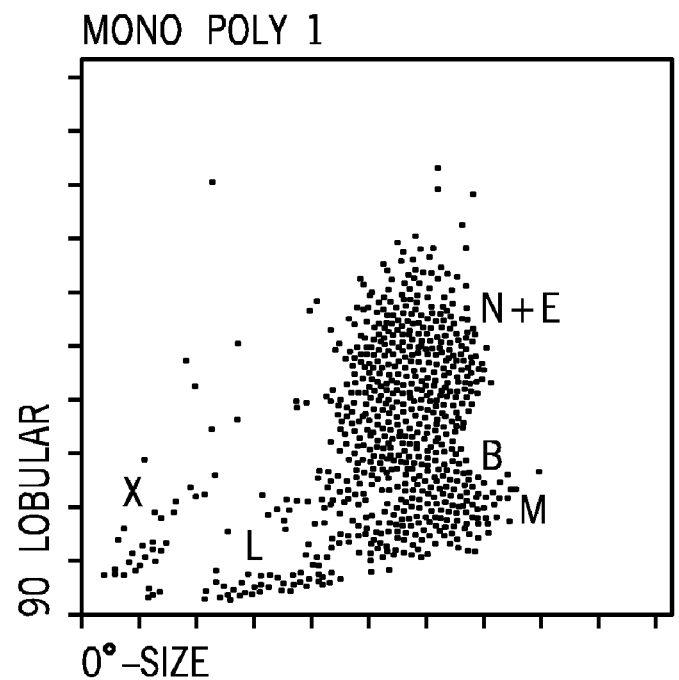
FIG. 7C is a cytogram of a clinical sample from the same CSF as in FIG. 7A, except that the X-axis corresponds to ALL signals and the Y-axis corresponds to PSS signals, as measured by the apparatus depicted in FIGS. 1 and 2.

FIG. 7C is a cytogram of a clinical sample from the same CSF as in FIG. 7A, except that the X-axis corresponds to ALL signals and the Y-axis corresponds to PSS signals, as measured by the apparatus depicted in FIGS. 1 and 2. The side scatter signals (PSS) from bacteria are much more noticeable in FIG. 7C than those of erythroblast nuclei in FIG. 4C.

Figure 7D:
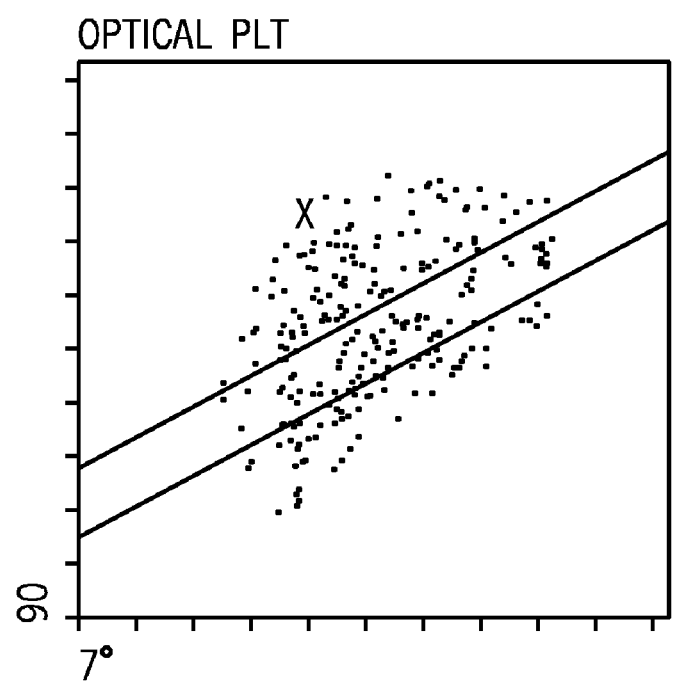
FIG. 7D is a cytogram of a clinical sample from the same CSF as in FIG. 7A, except that the signals are from the PLT channel, wherein the X-axis corresponds to IAS signals and the Y-axis corresponds to PSS signals, as measured by the apparatus depicted in FIGS. 1 and 2.

FIG. 7D is a cytogram of a clinical sample from the same CSF as in FIG. 7A, except that the signals are from the PLT channel, wherein the X-axis corresponds to IAS signals and the Y-axis corresponds to PSS signals, as measured by the apparatus depicted in FIGS. 1 and 2. In the optical platelet channel, the bacterial signals appear as dispersed noise signals in both inside and outside of the two floating platelet thresholds, as can be seen in FIG. 7D. FIG. 7C shows small ALL signals that fall below channel 25, but the PSS signals from the bacteria are much more visible than those of erythroblasts.

Example 3

The same method and apparatus that were used in COMPARATIVE EXAMPLE A were used to carry out EXAMPLE 3.

Figure 8A:
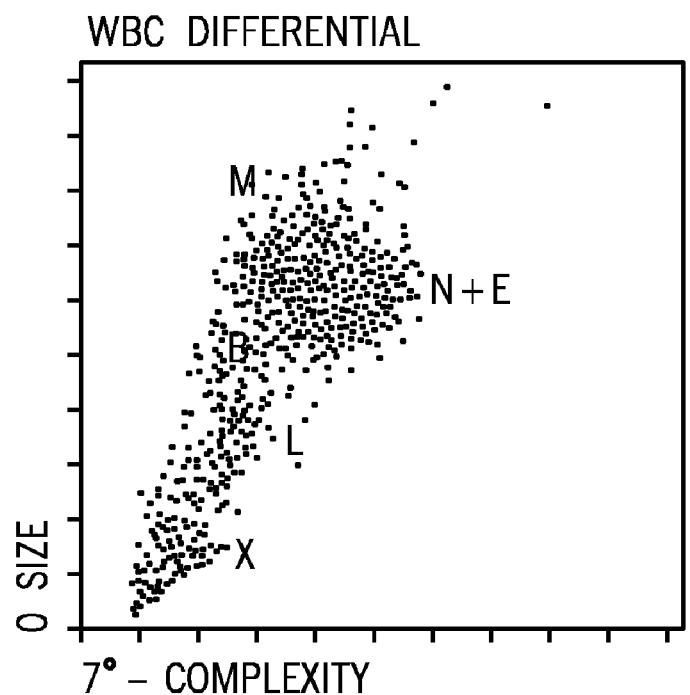
FIG. 8A is a cytogram of a clinical sample of a body fluid, intraperitoneal dialysate, from a male patient having a diagnosis of peritonitis. The X-axis corresponds to IAS signals and the Y-axis corresponds to ALL signals, as measured by the apparatus depicted in FIGS. 1 and 2.

FIG. 8A is a cytogram of a clinical sample of a body fluid, intraperitoneal dialysate, from a 57-year old male patient having a diagnosis of peritonitis. The X-axis corresponds to IAS signals and the Y-axis corresponds to ALL signals, as measured by the apparatus depicted in FIGS. 1 and 2.

The concentration of white blood cells is $1.43 \times 10^3/\mu L$, the concentration of red blood cells is $0.002 \times 10^6/\mu L$, neutrophils (83.4%), lymphocytes (8.75%), monocytes (6.95%), and eosinophils (0.89%).

Figure 8B:
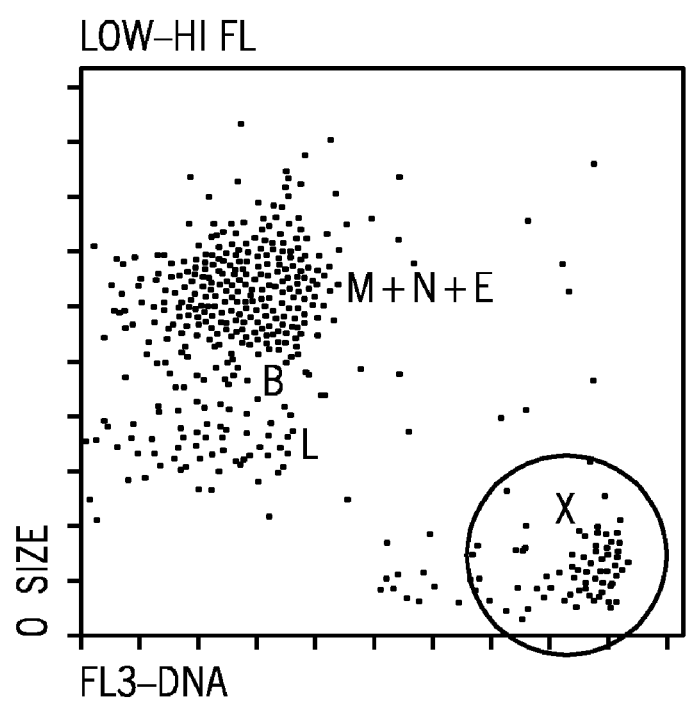
FIG. 8B is a cytogram of a clinical sample from the same body fluid as in FIG. 8A, except that the X-axis corresponds to FL3 signals and the Y-axis corresponds to ALL signals, as measured by the apparatus depicted in FIGS. 1 and 2.

FIG. 8B is a cytogram of a clinical sample from the same body fluid as in FIG. 8A, except that the X-axis corresponds to FL3 signals and the Y-axis corresponds to ALL signals, as measured by the apparatus depicted in FIGS. 1 and 2. The brightly stained dots in the circle at lower right corner of FIG. 8B indicate the presence of bacteria in this sample.

Figure 8C:
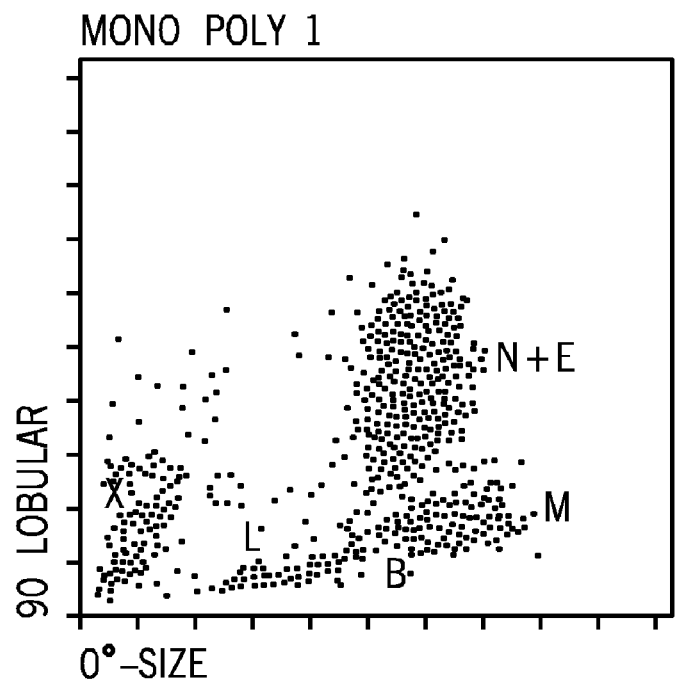
FIG. 8C is a cytogram of a clinical sample from the same body fluid as in FIG. 8A, except that the X-axis corresponds to ALL signals and the Y-axis corresponds to PSS signals, as measured by the apparatus depicted in FIGS. 1 and 2.

FIG. 8C is a cytogram of a clinical sample from the same body fluid as in FIG. 8A, except that the X-axis corresponds to ALL signals and the Y-axis corresponds to PSS signals, as measured by the apparatus depicted in FIGS. 1 and 2. The presence of bacteria in this sample is indicated by the PSS signals from the small particles in FIG. 8C at the lower end of the X-axis and the lower end of the Y-axis.

Figure 8D:
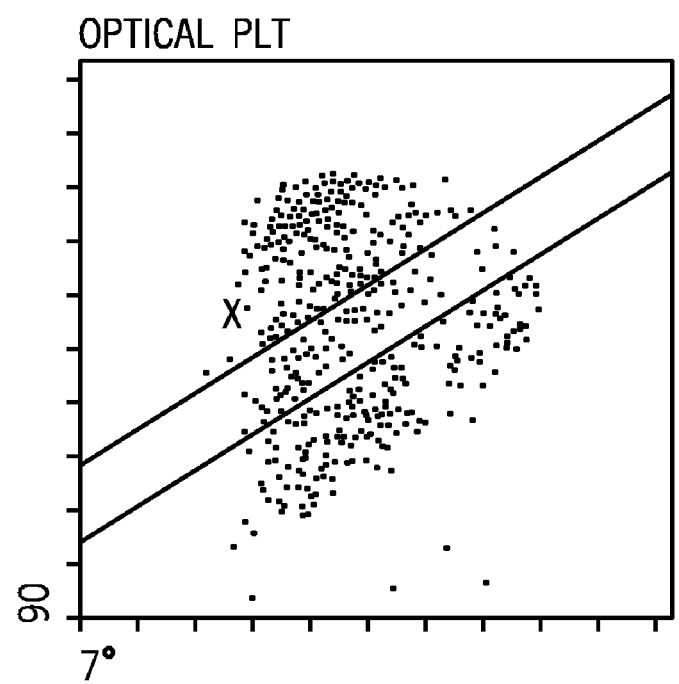
FIG. 8D is cytogram of a clinical sample of the same body fluid as in FIG. 8A, except that the signals are from the PLT channel, wherein the X-axis corresponds to IAS signals and the Y-axis corresponds to PSS signals, as measured by the apparatus depicted in FIGS. 1 and 2.

FIG. 8D is cytogram of a clinical sample of the same body fluid as in FIG. 8A, except that the signals are from the PLT channel, wherein the X-axis corresponds to IAS signals and the Y-axis corresponds to PSS, as measured by the apparatus depicted in FIGS. 1 and 2. In FIG. 8D, small particles appear as heavy noise signals in the platelet channel, both inside and outside of the two floating platelet thresholds.

Example 4

The same method and apparatus that were used in COMPARATIVE EXAMPLE A were used to carry out EXAMPLE 4.

Figure 9A:
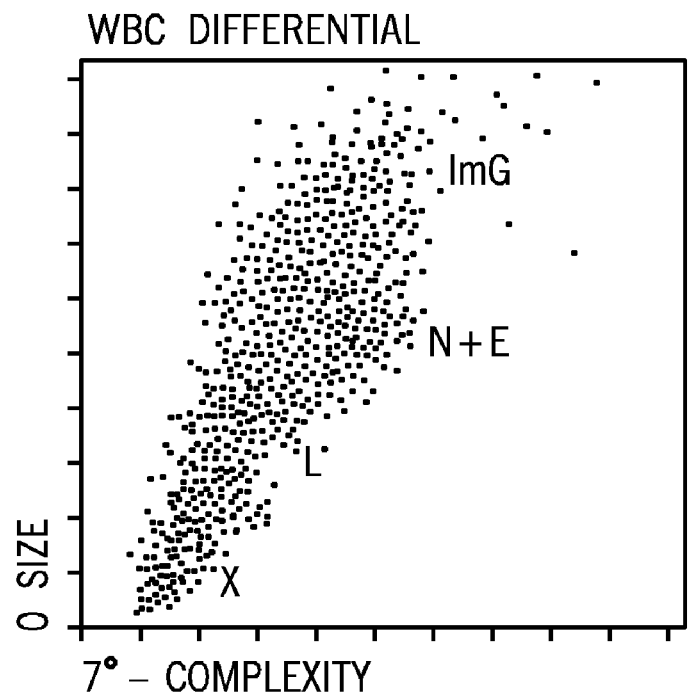
FIG. 9A is a cytogram of a clinical sample of a body fluid, intraperitoneal dialysate, from a female patient having a diagnosis of Actinobacterial infection. The X-axis corresponds to IAS signals and the Y-axis corresponds to ALL signals, as measured by the apparatus depicted in FIGS. 1 and 2.

FIG. 9A is a cytogram of a clinical sample of a body fluid, intraperitoneal dialysate, from a 60-year old female patient having a diagnosis of CAPD-peritonitis with Actinobacterial infection. The X-axis corresponds to IAS signals and the Y-axis corresponds to ALL signals, as measured by the apparatus depicted in FIGS. 1 and 2. The concentration of white blood cells is $10.30 \times 10^3/\mu L$, the concentration of red blood cells is $0.001 \times 10^6/\mu L$, neutrophils (60.4%), lymphocytes (11.8%), monocytes (8.32%), and eosinophils (0.69%).

Figure 9B:
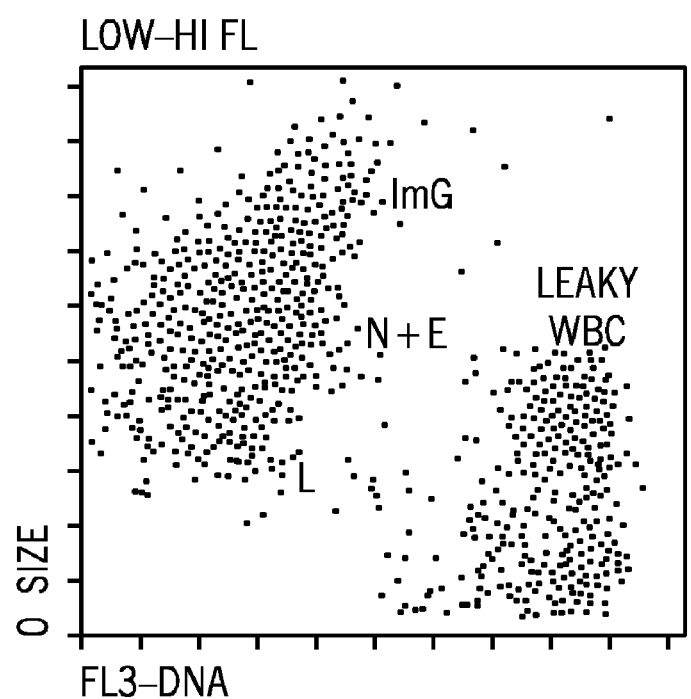
FIG. 9B is a clinical sample of the same body fluid as in FIG. 9A, except that the X-axis corresponds to FL3 signals and the Y-axis corresponds to ALL signals, as measured by the apparatus depicted in FIGS. 1 and 2.

FIG. 9B is a clinical sample of the same body fluid as in FIG. 9A, except that the X-axis corresponds to FL3 signals and the Y-axis corresponds to ALL signals, as measured by the apparatus depicted in FIGS. 1 and 2. The brightly stained FL3+ dots in the circle at lower right corner of FIG. 9B indicate the bacteria.

Figure 9C:
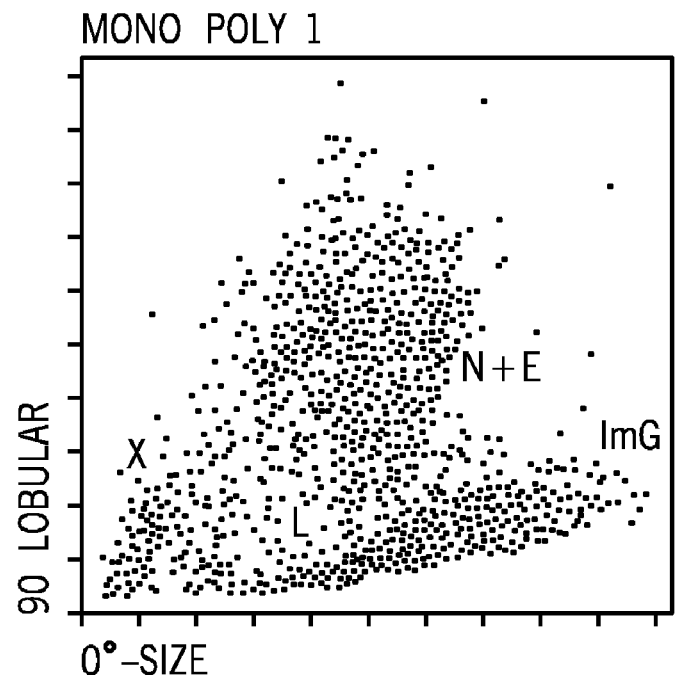
FIG. 9C is a clinical sample of the same body fluid as in 9A, except that the X-axis corresponds to ALL signals and the Y-axis corresponds to PSS signals, as measured by the apparatus depicted in FIGS. 1 and 2.
Figure 9D:
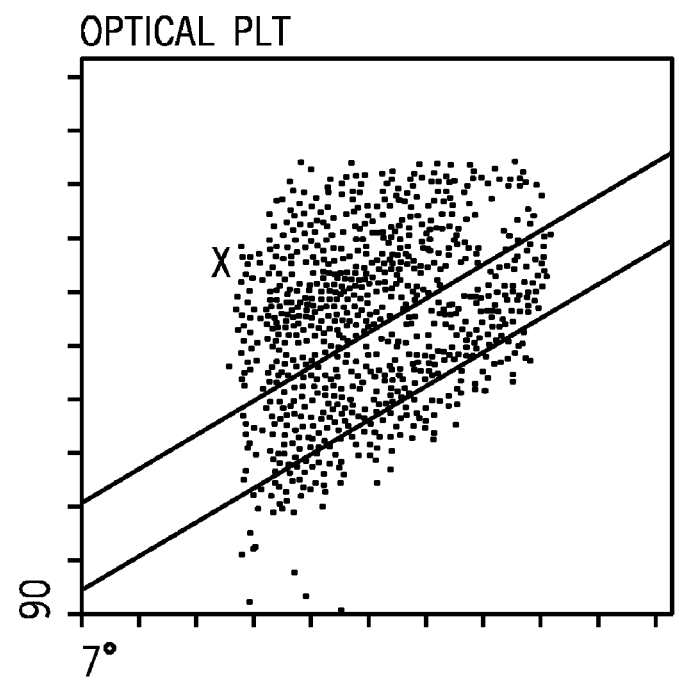
FIG. 9D is a clinical sample of the same body fluid as in FIG. 9A, except that the signals are from the PLT channel, wherein the X-axis corresponds to IAS signals and the Y-axis corresponds to PSS signals, as measured by the apparatus depicted in FIGS. 1 and 2.

FIG. 9C is a clinical sample of the same body fluid as in 9A, except that the X-axis corresponds to ALL signals and the Y-axis corresponds to PSS signals, as measured by the apparatus depicted in FIGS. 1 and 2. FIG. 9D is a clinical sample of the same body fluid as in FIG. 9A, except that the signals are from the PLT channel, wherein the X-axis corresponds to IAS signals and the Y-axis corresponds to PSS signals, as measured by the apparatus depicted in FIGS. 1 and 2.

PSS signals from bacteria in both the white blood cell channel (FIG. 9C) and the optical platelet channel (FIG. 9D) are apparent. In FIG. 9D, very dense bacterial signals are seen as dispersed noise signals generally outside, but also inside, of the two floating platelet thresholds.

Example 5

The same method and apparatus that were used in COMPARATIVE EXAMPLE A were used to carry out EXAMPLE 5.

Figure 10A:
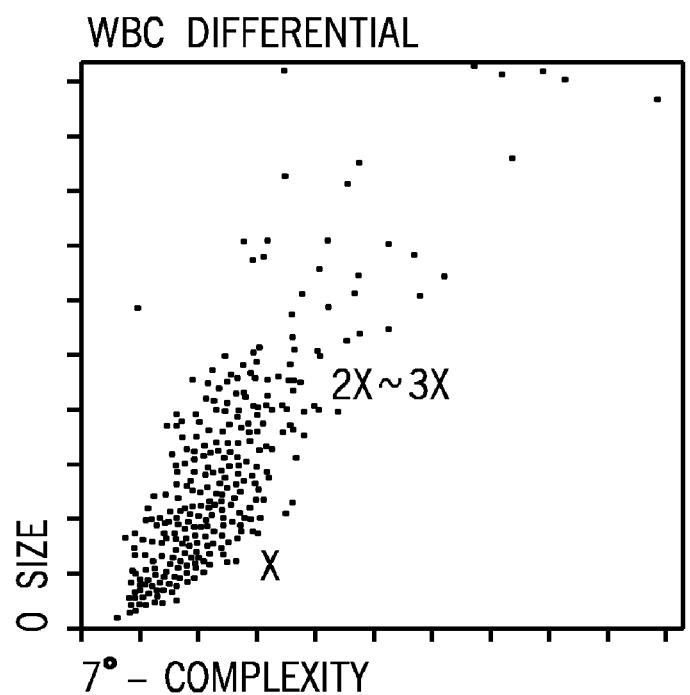
FIG. 10A is a cytogram of a clinical sample of CSF from a patient having a diagnosis of complicated pancreatitis due to coagulase-negative streptococcus. The X-axis corresponds to IAS signals and the Y-axis corresponds to ALL signals, as measured by the apparatus depicted in FIGS. 1 and 2.
Figure 10B:
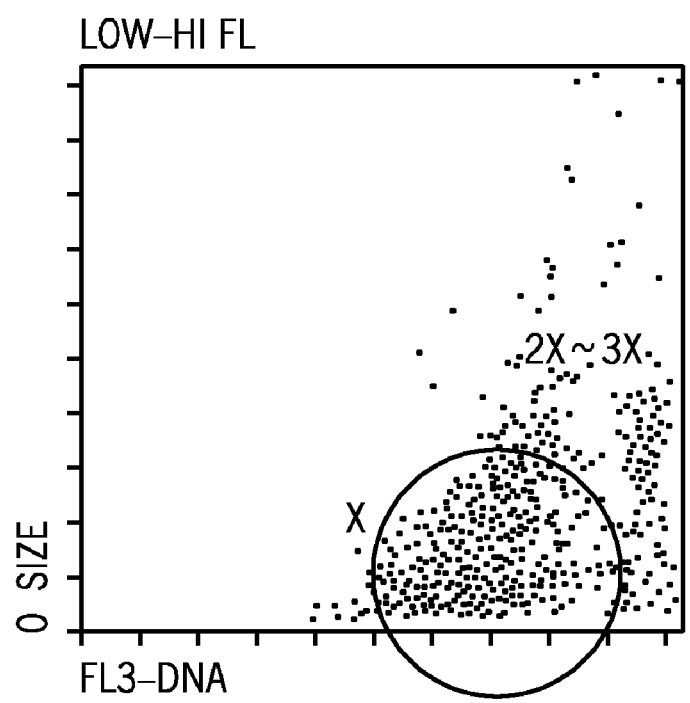
FIG. 10B is a cytogram of a clinical sample of the same CSF as in FIG. 10A, except that the X-axis corresponds to FL3 signals and the Y-axis corresponds to ALL signals, as measured by the apparatus depicted in FIGS. 1 and 2.
Figure 10C:
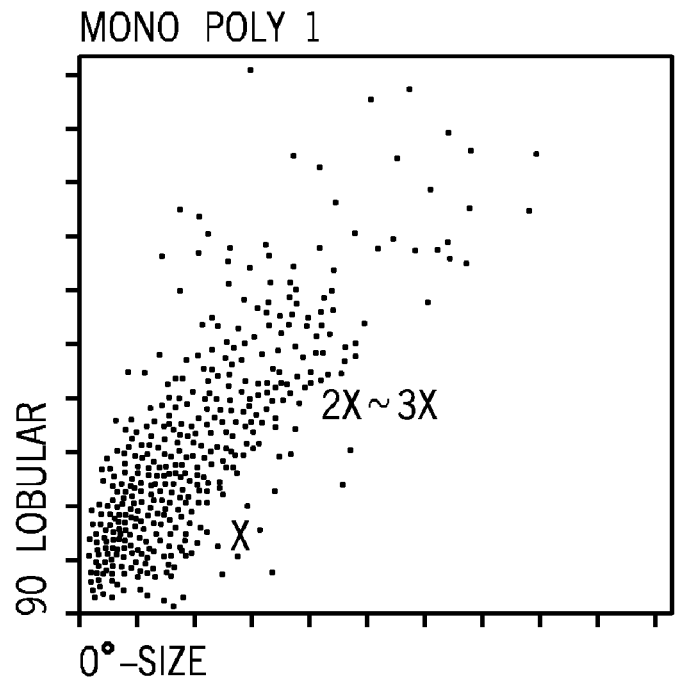
FIG. 10C is a cytogram of a clinical sample of the same CSF as in FIG. 10A, except that the X-axis corresponds to ALL signals and Y-axis corresponds to PSS signals, as measured by the apparatus depicted in FIGS. 1 and 2.
Figure 10D:
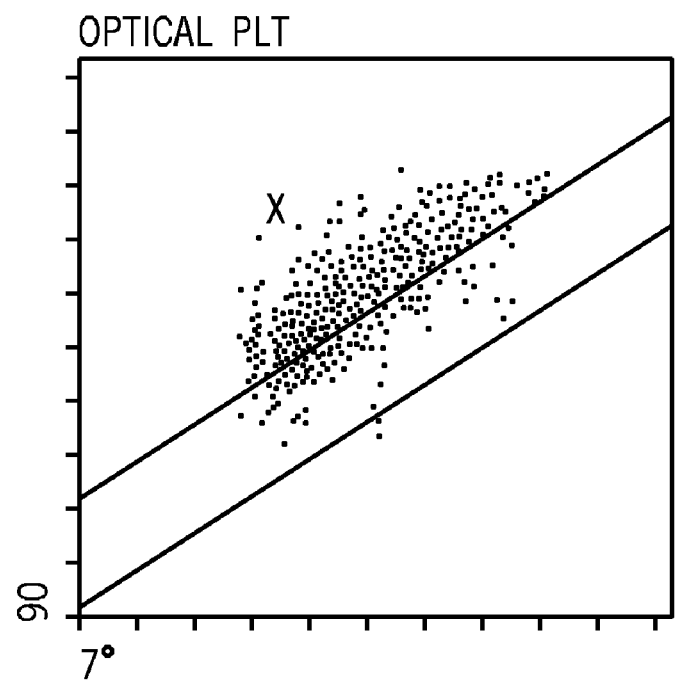
FIG. 10D is a cytogram of a clinical sample of the same CSF as in FIG. 10A, except that the signals are from the PLT channel, wherein the X-axis corresponds to IAS signals and the Y-axis corresponds to PSS signals, as measured by the apparatus depicted in FIGS. 1 and 2.

FIG. 10A is a cytogram of a clinical sample of CSF from a 63-year old female patient having a diagnosis of complicated pancreatitis due to coagulase-negative streptococcus (CNS) infection. The X-axis corresponds to IAS signals and the Y-axis corresponds to ALL signals, as measured by the apparatus depicted in FIGS. 1 and 2. FIG. 10B is a cytogram of a clinical sample of the same CSF as in FIG. 10A, except that the X-axis corresponds to FL3 signals and the Y-axis corresponds to ALL signals, as measured by the apparatus depicted in FIGS. 1 and 2. FIG. 10C is a cytogram of a clinical sample of the same CSF as in FIG. 10A, except that the X-axis corresponds to ALL signals and Y-axis corresponds to PSS signals, as measured by the apparatus depicted in FIGS. 1 and 2. FIG. 10D is a cytogram of a clinical sample of the same CSF as in FIG. 10A, except that the signals are from the PLT channel, wherein the X-axis corresponds to IAS signals and the Y-axis corresponds to PSS signals, as measured by the apparatus depicted in FIGS. 1 and 2.

Very dense FL3+ bacterial signals below ALL channel 25-30 (see circle in FIG. 10B) and PSS signals in both the white blood cell channel (FIG. 10C) and the platelet channel (FIG. 10D) are clearly visible. In the optical platelet channel, a dense streak of bacterial signals is seen just above the upper platelet threshold.

The apparatus and the reagent system described herein can be used to eliminate cell debris and qualify signals that are smaller than the nuclei of erythroblasts, such as those from bacteria because their genetic material, such as RNA or DNA nuclei, are stained by the reagent system, and the triple-trigger circuitry validates bacterial signals even if their size signals, ALL, fall below the ALL trigger, because their FL3 signals are much higher than the FL3 trigger.

As illustrated in FIGS. 7A, 7B, 7C, 7D, 8A, 8B, 8C, 8D, 9A, 9B, 9C, 9D, 10A, 10B, 10C, and 10D, signal patterns for ALL, IAS, PSS, and FL3 and the location of bacterial signals differ from those of subsets of white blood cells and erythroblasts; consequently, bacterial signals can easily be identified by the algorithm(s) of the system by using appropriate logic for cell size, fluorescence intensity, and the pattern and the location of the clusters.

In another embodiment, samples of certain body fluids, such as, for example, synovial fluid, can be pretreated with a viscosity reducing agent, such as, for example, hyaluronidase, for a short period of time, to reduce the viscosity of the sample of the body fluid prior to analyzing the sample on the system Open Mode. After the sample is mixed with the reagent system, which is designed to preserve white blood cells, cell surface antigens for immunophenotyping, and at the same time lyse red blood cells, if any red blood cells are present in the sample, the membranes of erythroblasts, if any erythroblasts are present in the sample, and stain the nuclei of erythroblasts, if any nuclei of erythroblasts are present in the sample, and bacteria, the prepared cells are passed through the electro-optical system described in FIG. 1 in single file. The electronic logic, triple-triggering circuitry of the system and the algorithm(s) of the system differentiate each cell population based on cell volume, complexity of cells, lobularity of cells, refractive index of cells, fluorescence intensity, and the location and pattern of each cell population. The triple-triggering circuitry eliminates small signals generated by cell debris and validates bacterial signals, i.e., <ALL trigger,>FL3 and IAS trigger. The algorithm(s) of the system will differentiate bacterial signals from those of erythroblasts by the size of the ALL signal, the intensity of the FL3+ signals from bacteria, and the shape and the number of FL3 clusters, i.e., the characteristic two clusters for erythroblasts, which stand in contrast to a single loosely distributed cluster for bacterial signals.

In yet another embodiment, body fluids can be run on an automatic mode if a sufficient volume of the sample of the body fluid is available to use the automatic mode. Body fluids are processed in the automatic mode in the manner described previously, for the open mode, except that the sample of the body fluid is presented directly to the automated instrument by a robotic mechanism.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method of differentiating bacteria from white blood cells or erythroblasts in a body fluid, the method comprising the steps of:
   (a) providing an automated hematology analyzer capable of measuring multi-angle light scatter and fluorescence, the automated hematology analyzer having a triple-trigger circuit including an ALL trigger, an FL3 trigger, an IAS trigger, an OR gate, and an AND gate;
   (b) providing a reagent capable of lysing red blood cells, the reagent also capable of preserving morphology of white blood cells;
   (c) providing a sample of the body fluid;
   (d) mixing the reagent and the sample of the body fluid;
   (e) lysing red blood cells and membranes of erythroblasts;
   (f) staining erythroblast nuclei with a nuclear stain;
   (g) detecting white blood cells within the sample of the body fluid by measuring multi-angle light scatter with the hematology analyzer;
   (h) detecting erythroblast nuclei within the sample of the body fluid by measuring at least one of multi-angle light scatter and fluorescence with the hematology analyzer; and
   (i) detecting bacteria within the sample of the body fluid by measuring fluorescence and multi-angle light scatter of a bacteria signal with the hematology analyzer, wherein the bacteria signal is generated by bacteria within the sample of the body fluid, and wherein the bacteria signal is qualified as a valid bacteria signal if an amplitude of the bacteria signal is below the OR gate and ALL trigger, but above the AND gate, FL3 trigger, and IAS trigger.

2. The method of claim 1, further comprising:
diluting the sample of the body fluid with a diluent.

3. The method of claim 1, further comprising:
detecting and counting red blood cells.

4. The method of claim 1, further comprising:
transporting a lysed sample of the body fluid through a flow cell.

5. The method of claim 1, further comprising:
storing data for the analysis of the sample of the body fluid.

6. The method of claim 1, further comprising:
reporting results for the analysis of the sample of the body fluid.

7. The method of claim 1, further comprising:
analyzing the sample of the body fluid by at least one algorithm to differentiate white blood cells, erythrocytes, and bacteria from each other.

8. The method of claim 1, wherein erythroblasts and bacteria are counted by multi-angle scatter measurements and fluorescence measurements with the hematology analyzer.

9. The method of claim 1, wherein at least one multi-angle light scatter measurement is obtained at an angle of from about 0° to about 1° with the hematology analyzer.

10. The method of claim 1, wherein at least one multi-angle light scatter parameter threshold of the hematology analyzer is set to qualify all signals from white blood cells and discriminate all other signals.

11. The method of claim 1, wherein at least one multi-angle light scatter measurement is obtained at an angle of from about 3° to about 10° with the hematology analyzer.

12. The method of claim 1 wherein at least one multi-angle light scatter parameter threshold of the hematology analyzer and at least one fluorescence threshold of the hematology analyzer are set to eliminate spurious positive noise signals from said at least one fluorescence threshold, and to eliminate spurious negative noise signals from said at least one fluorescence threshold, and to include signals from white blood cells, erythroblasts, and bacteria populations in the signals obtained.

13. The method of claim 12, further comprising:
constructing a three-dimensional plot of intensity signals of said at least one fluorescence threshold and scattered light from at least one multi-angle light scatter parameter threshold of the hematology analyzer to obtain and qualify signals.

14. The method of claim 13, further comprising:
differentiating white blood cells, erythroblasts, and bacteria, from each other, from the constructed three-dimensional plot and the qualified signals, and determining the number of cells of said white blood cells, erythroblasts, and bacteria.

15. The method of claim 1, wherein said body fluid is selected from the group consisting of: blood, cerebrospinal fluid, pleural fluid, peritoneal fluid, pericardial fluid, synovial fluid, ascites fluid, drain fluid, and dialysate fluid.

16. The method of claim 15, further comprising:
using a viscosity reducing agent to reduce the viscosity of said body fluid.

17. The method of claim 1, further comprising:
differentiating bacteria from erythroblasts within the sample of the body fluid based on a size of an ALL signal, an intensity of an FL3+signal, and a shape and a number of FL3 clusters.

18. A method of differentiating between cell debris, white blood cells, erythroblasts, and bacteria in a body fluid sample, the method comprising:
(a) providing an automated hematology analyzer capable of measuring multi-angle light scatter and fluorescence, the automated hematology analyzer having a triple trigger circuit including an ALL trigger, an FL3 trigger, an IAS trigger, an OR gate, and an AND gate;
(b) configuring the triple trigger circuit to eliminate signals from cell debris and qualify signals from white blood cells, erythroblasts, and bacteria;
(c) providing a body fluid sample;
(d) mixing a lysing reagent with the body fluid sample to lyse red blood cells and membranes of erythroblasts;
(e) staining erythroblast nuclei with a nuclear stain;
(f) analyzing the body fluid sample with the automated hematology analyzer;
(g) qualifying a bacteria signal generated by bacteria within the body fluid sample, wherein the bacteria signal is qualified based on the triple trigger circuit configuration, and wherein the qualified bacteria signal includes an ALL signal, an FL3+signal, and FL3 clusters; and
(h) differentiating bacteria from cell debris, white blood cells, or erythroblasts based on a size of the ALL signal, an intensity of the FL3+signal, and a shape and a number of the FL3 clusters.

19. A method of differentiating between white blood cells, erythroblasts, and bacteria in a body fluid sample, using a hematology analyzer capable of measuring multi-angle light scatter and fluorescence, wherein the hematology analyzer includes a triple trigger circuit having an ALL trigger, an FL3 trigger, an IAS trigger, an OR gate, and an AND gate, the method comprising:
detecting bacteria within the sample by measuring multi-angle light scatter and fluorescence of a bacteria signal with the hematology analyzer, wherein the bacteria signal is generated by bacteria within the sample, and wherein an amplitude of the bacteria signal is below the OR gate and ALL trigger, but above the AND gate, FL3 trigger, and IAS trigger; and
differentiating the bacteria within the sample based on a size of an ALL signal measured by the hematology analyzer, an intensity of an FL3+signal measured by the hematology analyzer, and a shape and a number of FL3 clusters measured by the hematology analyzer.

20. A method of detecting bacteria in a body fluid sample, using a hematology analyzer capable of measuring multi-angle light scatter and fluorescence, wherein the hematology analyzer includes a triple trigger circuit having an ALL trigger, an FL3 trigger, an IAS trigger, an OR gate, and an AND gate, the method comprising:
measuring fluorescence and multi-angle light scatter of a signal with the hematology analyzer;
determining whether the signal is generated by bacteria within the sample by determining whether an amplitude of the signal is below the OR gate and ALL trigger, but above the AND gate, FL3 trigger, and IAS trigger; and
detecting bacteria within the sample based on a size of an ALL signal measured by the hematology analyzer, an intensity of an FL3+signal measured by the hematology analyzer, and a shape and a number of FL3 clusters measured by the hematology analyzer.

* * * * *